United States Patent
Evans et al.

(10) Patent No.: US 12,064,480 B2
(45) Date of Patent: Aug. 20, 2024

(54) IMMUNIGENIC ALPHA-BRANCHED TREHALOSE-DIESTERS

(71) Applicant: GLAXOSMITHKLINE BIOLOGICALS SA, Rixensart (BE)

(72) Inventors: Jay T Evans, Hamilton, MT (US); Alyson Smith, Hamilton, MT (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 872 days.

(21) Appl. No.: 17/046,595

(22) PCT Filed: Apr. 12, 2019

(86) PCT No.: PCT/EP2019/059385
§ 371 (c)(1),
(2) Date: Oct. 9, 2020

(87) PCT Pub. No.: WO2019/197595
PCT Pub. Date: Oct. 17, 2019

(65) Prior Publication Data
US 2021/0077618 A1  Mar. 18, 2021

Related U.S. Application Data

(60) Provisional application No. 62/657,078, filed on Apr. 13, 2018.

(51) Int. Cl.
C07H 13/04 (2006.01)
A61K 39/04 (2006.01)
(Continued)

(52) U.S. Cl.
CPC .............. *A61K 39/39* (2013.01); *A61K 39/04* (2013.01); *A61P 31/06* (2018.01); *A61P 37/04* (2018.01);
(Continued)

(58) Field of Classification Search
CPC ....................................................... C07H 13/04
See application file for complete search history.

(56) References Cited

U.S. PATENT DOCUMENTS 4,307,229 A  12/1981  Liav et al.
4,684,719 A  8/1987  Nishikawa et al.
(Continued)

FOREIGN PATENT DOCUMENTS

DE  3241199 C2  8/1987
EP  2123662 A1  11/2009
(Continued)

OTHER PUBLICATIONS

Boothroyd et al., "Why Do Some Molecules Form Hydrates or Solvates?" Crystal Growth and Design vol. 18 pp. 1903-1908 DOI: 10.1021/acs.cgd.8b00160 (Year: 2018).*
(Continued)

*Primary Examiner* — Eric Olson
(74) *Attorney, Agent, or Firm* — Birch, Stewart, Kolasch & Birch, LLP

(57) ABSTRACT

The invention relates to compounds of formula (I) and their use in eliciting a pro-Th17 immune response. Further provided are methods of production of said compounds. (Formula I) wherein m is an integer between 4 and 13; n is an
(Continued)

integer between 4 and 13; x is an integer between 4 and 13; y is an integer between 4 and 13.

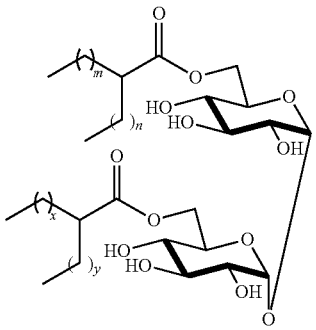

1 Claim, 6 Drawing Sheets

Specification includes a Sequence Listing.

(51) Int. Cl.
  A61K 39/39 (2006.01)
  A61P 31/06 (2006.01)
  A61P 37/04 (2006.01)
  C07H 13/06 (2006.01)
  A61K 39/00 (2006.01)
(52) U.S. Cl.
  CPC ............ *C07H 13/04* (2013.01); *C07H 13/06* (2013.01); *A61K 2039/55511* (2013.01)

(56) References Cited

U.S. PATENT DOCUMENTS

| | | | |
|---|---|---|---|
| 4,720,456 | A | 1/1988 | Wagner et al. |
| 4,803,070 | A | 2/1989 | Cantrell et al. |
| 4,814,436 | A | 3/1989 | Shibata et al. |
| 5,049,664 | A | 9/1991 | Yoshinaga et al. |
| 8,163,713 | B2 | 4/2012 | Nishizawa et al. |
| 8,563,009 | B2 | 10/2013 | Agger et al. |
| 8,741,871 | B2 | 6/2014 | Nishizawa et al. |
| 2010/0093993 | A1 | 4/2010 | Nishizawa et al. |
| 2010/0249057 | A1 | 9/2010 | Nishizawa et al. |
| 2011/0218171 | A1 | 9/2011 | Nishizawa et al. |

FOREIGN PATENT DOCUMENTS

| | | |
|---|---|---|
| GB | 2133399 A | 7/1984 |
| WO | WO 2006/002642 A2 | 1/2006 |
| WO | WO 2007/111214 A1 | 10/2007 |
| WO | WO 2008/093700 A1 | 8/2008 |
| WO | WO 2009/003474 A1 | 1/2009 |
| WO | WO 2010/050178 A1 | 5/2010 |
| WO | WO 2019/165114 A1 | 8/2019 |
| WO | WO 2019/169313 A1 | 9/2019 |

OTHER PUBLICATIONS

Xin et al., "Solvate Prediction for Pharmaceutical Organic Molecules with Machine Learning" Crystal Growth and Design vol. 19 pp. 1903-1911 DOI: 10.1021/acs.cgd.8b01883 (Year: 2018).*

Morisette et al., "High-throughput crystallization: polymorphs, salts, co-crystals and solvates of pharmaceutical solids" Advanced Drug Delivery Reviews vol. 56 pp. 275-300 doi:10.1016/j.addr.2003.10.020 (Year: 2004).*

Silverman et al., "Prodrugs and Drug Delivery Systems", The Organic Chemistry of Drug Design and Drug Action, Published by Academic Press, ISBN 0-12-643730-0 (Year: 1992).*

Yamamoto et al., "Development of Vizantin, a Safe Immunostimulant, Based on the Structure-Activity Relationship of Trehalose-6,6'-dicorynomycolate" Journal of Medicinal Chemistry vol. 56 pp. 381-385 (Year: 2013).*

Decout et al., "Rational design of adjuvants targeting the C-type lectin Mincle," PNAS, vol. 114, No. 10, Mar. 7, 2017, pp. 2675-2680.

Durand et al., "Phase Behaviour of Cord Factor and Related Bacterial Glycolipid Toxins," Eur. J. Biochem., vol. 93, 1979, pp. 103-112.

Durand et al., "Property and Activity of Mycoloyl Esters of Methyl Glucoside and Trehalose," Eur. J. Biochem., vol. 94, 1979, pp. 109-118.

Foster et al., "Lipidated Brartemicin Analogues Are Potent Th1-Stimulating Vaccine Adjuvants," J. Med. Chem., vol. 61, 2018, pp. 1045-1060.

Huber et al., "Trehalose diester glycolipids are superior to the monoesters in binding to Mincle, activation of macrophages in vitro and adjuvant activity in vivo," Innate Immunity, vol. 22, No. 6, 2016, pp. 405-418.

Johnson et al., "An Efficient Synthesis of 6,6'-DI-O-acylated α,α-Trehaloses," J. Carbohydrate Chemistry, vol. 17, No. 6, 1998, pp. 969-974.

Kallerup et al., "Influence of trehalose 6,6'-diester (TDX) chain length on the physicochemical and immunopotentiating properties of DDA/TDX liposomes," European Journal of Pharmaceutics and Biopharmaceutics, vol. 90, 2015, 2015 (published online Nov. 11, 2014), pp. 80-89.

Khan et al., "Long-Chain Lipids Are Required for the Innate Immune Recognition of Trehalose Diesters by Macrophages," ChemBioChem, vol. 12, 2011, pp. 2572-2576.

Numata et al., "Lethal and Adjuvant Activities of Cord Factor (Trehalose-6,6'-dimycolate) and Synthetic Analogs in Mice," Chem. Pharm. Bull., vol. 33, No. 10, 1985, pp. 4544-4555.

Prabhakar et al., "A fully enzymatic esterification/transesterification sequence for the preparation of symmetrical and unsymmetrical trehalose diacyl conjugates," Green Chemistry, vol. 19, 2017, pp. 987-995.

Ryter et al., "Aryl Trehalose Derivatives as Vaccine Adjuvants for Mycobacterium tuberculosis," J. Med. Chem., vol. 63, 2020, pp. 309-320.

Smith et al., "Species-Specific Structural Requirements of Alpha-Branched Trehalose Diester Mincle Agonists," Frontiers in Immunology, vol. 10, Article 338, Feb. 2019, pp. 1-13.

Van der Peet et al., "Corynomycolic acid-containing glycolipids signal through the pattern recognition receptor Mincle," Chem. Commun., vol. 51, 2015, pp. 5100-5103.

Van der Peet et al., "Lipid structure influences the ability of glucose monocorynomycolate to signal through Mincle," Org. Biomol. Chem., vol. 14, 2016, pp. 9267-9277.

Yamamoto et al., "Development of Vizantin, a Safe Immunostimulant, Based on the Structure-Activity Relationship of Trehalose-6,6'-dicorynomycolate," J. Med. Chem., vol. 56, Dec. 4, 2012, pp. 381-385.

* cited by examiner

Figure 3A

| SampleID | IL-1b (pg/ml) | IL-6 (pg/ml) | IL-12p70 (pg/ml) | TNF-a (pg/ml) | IL-23 (pg/ml) | IFN-g (pg/ml) | SampleID | IL-1b (pg/ml) |
|---|---|---|---|---|---|---|---|---|
| Std01 | 5.6503 | 4.5819 | 97.7040 | 4.6732 | 76.4497 | 2.3800 | Std01 | 5.48 |
| Std02 | 16.1557 | 14.2081 | 287.0741 | 13.9770 | 261.2016 | 7.3278 | Std02 | 18.32 |
| Std03 | 55.2793 | 41.4315 | 918.7040 | 43.7956 | 727.6871 | 22.1104 | Std03 | 47.86 |
| Std04 | 139.2005 | 117.7193 | 2484.3984 | 118.1865 | 1958.2466 | 60.0929 | Std04 | 146.71 |
| Std05 | 485.7758 | 423.4305 | 8293.1205 | 406.3868 | 7057.5419 | 212.7137 | Std05 | Rejected |
| Std06 | 1320.3317 | 1044.7888 | 23117.6360 | 1103.6987 | 19353.4184 | 565.9658 | Std06 | 1392.88 |
| Std07 | 4122.4616 | 3471.9559 | 71665.6112 | 3451.8874 | 58371.3866 | 1767.5185 | Std07 | 4072.44 |
| Blank01 | 0 | 0 | 0 | 0 | 0 | 0 | Blank01 | 0.34 |
| TDE | [ ] | | IL1B | IL6 | 12p70 | TNF | IL23 | IFN |
| B4 | 200 | 1 | 5.1 | 55.4 | 0.0 | 56.9 | 6.2 | 0.0 |
| B4 | 66.6 | 2 | 4.4 | 55.4 | 0.0 | 35.3 | 6.2 | 0.0 |
| B4 | 22.2 | 3 | 4.9 | 48.1 | 0.0 | 43.4 | 31.1 | 0.0 |
| B4 | 7.4 | 4 | 2.6 | 38.1 | 0.0 | 23.6 | 6.2 | 0.0 |
| B4 | 2.4 | 5 | 4.1 | 44.5 | 0.0 | 31.9 | 31.1 | 0.0 |
| B4 | 0.8 | 6 | 10.7 | 86.4 | 0.0 | 34.9 | 6.2 | 0.0 |
| B4 | 0.27 | 7 | 4.4 | 31.0 | 0.0 | 24.0 | 6.2 | 0.0 |
| B4 | 0 | 8 | 6.4 | 34.3 | 0.0 | 25.9 | 6.2 | 0.0 |
| B6 | 200 | 9 | 35.2 | 273.4 | 0.0 | 80.3 | 6.2 | 0.0 |
| B6 | 66.6 | 10 | 6.7 | 71.2 | 0.0 | 37.9 | 31.1 | 0.0 |
| B6 | 22.2 | 11 | 7.8 | 65.6 | 0.0 | 56.6 | 6.2 | 0.0 |
| B6 | 7.4 | 12 | 7.0 | 45.0 | 0.0 | 32.3 | 6.2 | 0.0 |
| B6 | 2.4 | 13 | 3.1 | 44.5 | 0.0 | 31.2 | 31.1 | 0.0 |
| B6 | 0.8 | 14 | 2.3 | 28.0 | 0.0 | 21.0 | 6.2 | 0.0 |
| B6 | 0.27 | 15 | 3.8 | 33.0 | 0.0 | 25.9 | 6.2 | 0.0 |
| B6 | 0 | 16 | 15.1 | 37.9 | 0.0 | 21.7 | 6.2 | 0.0 |
| B8 | 200 | 17 | 41.6 | 0.6 | 0.0 | 7.2 | 6.2 | 0.0 |
| B8 | 66.6 | 18 | 37291.1 | 60183.2 | 25.7 | 0.0 | 119.4 | 0.1 |
| B8 | 22.2 | 19 | 8.5 | 57.2 | 0.0 | 39.0 | 6.2 | 0.0 |
| B8 | 7.4 | 20 | 4.9 | 51.0 | 0.0 | 34.9 | 6.2 | 0.0 |
| B8 | 2.4 | 21 | 7.0 | 60.1 | 0.0 | 40.5 | 6.2 | 0.0 |
| B8 | 0.8 | 22 | 3.8 | 44.5 | 0.0 | 31.9 | 6.2 | 0.0 |
| B8 | 0.27 | 23 | 4.1 | 50.4 | 0.0 | 28.9 | 6.2 | 0.0 |
| B8 | 0 | 24 | 0.4 | 10.2 | 0.0 | 6.8 | 0.0 | 0.0 |
| B10 | 200 | 25 | 16097.1 | 13108.4 | 0.0 | 1440.2 | 76.4 | 0.5 |
| B10 | 66.6 | 26 | 771.3 | 7700.7 | 0.0 | 762.9 | 54.2 | 0.0 |
| B10 | 22.2 | 27 | 393.4 | 3387.4 | 0.0 | 756.5 | 31.1 | 0.0 |
| B10 | 7.4 | 28 | 46.3 | 343.5 | 0.0 | 137.5 | 6.2 | 0.0 |
| B10 | 2.4 | 29 | 33.4 | 313.7 | 0.0 | 119.2 | 31.1 | 0.0 |
| B10 | 0.8 | 30 | 11.8 | 90.5 | 0.0 | 36.4 | 6.2 | 0.0 |
| B10 | 0.27 | 31 | 6.4 | 44.5 | 0.0 | 30.8 | 6.2 | 0.0 |
| B10 | 0 | 32 | 5.7 | 26.2 | 0.0 | 27.8 | 6.2 | 0.0 |
| B14 | 200 | 33 | 350.4 | 515.6 | 0.0 | 83.5 | 6.2 | 0.0 |
| B14 | 66.6 | 34 | 13033.9 | 8529.0 | 0.0 | 508.8 | 54.2 | 0.1 |
| B14 | 22.2 | 35 | 0.0 | 26255.7 | 0.0 | 1540.1 | 119.4 | 0.9 |
| B14 | 7.4 | 36 | 256017.3 | 15600.1 | 0.0 | 1812.7 | 119.4 | 0.9 |
| B14 | 2.4 | 37 | 5288.9 | 13743.4 | 0.0 | 1047.4 | 119.4 | 0.1 |
| B14 | 0.8 | 38 | 9.6 | 59.3 | 0.0 | 40.5 | 6.2 | 0.0 |
| B14 | 0.27 | 39 | 27.4 | 113.5 | 0.0 | 62.7 | 6.2 | 0.0 |
| B14 | 0 | 40 | 11.2 | 25.4 | 0.0 | 28.2 | 6.2 | 0.0 |
| B16 | 200 | 41 | 18552.5 | 3500.6 | 0.0 | 2077.4 | 76.4 | 0.1 |
| B16 | 66.6 | 42 | 0.0 | 0.0 | 0.0 | 0.0 | 0.0 | 0.0 |
| B16 | 22.2 | 43 | 0.0 | 30870.8 | 0.0 | 2730.9 | 119.4 | 3.4 |
| B16 | 7.4 | 44 | 19535.4 | 12543.0 | 0.0 | 2074.0 | 140.3 | 0.1 |
| B16 | 2.4 | 45 | 47.2 | 56.7 | 0.0 | 51.8 | 6.2 | 0.0 |
| B16 | 0.8 | 46 | 9.4 | 52.0 | 0.0 | 42.0 | 6.2 | 0.0 |
| B16 | 0.27 | 47 | 6.7 | 39.9 | 0.0 | 36.8 | 6.2 | 0.0 |
| B16 | 0 | 48 | 9.1 | 24.7 | 0.0 | 28.2 | 0.0 | 0.0 |

Figure 3B

| | | | | | | | |
|---|---|---|---|---|---|---|---|
| B18 | 200 | 49 | 2074.8 | 1659.9 | 0.0 | 1566.1 | 54.2 | 0.0 |
| B18 | 66.6 | 50 | 10781.8 | 19501.5 | 0.0 | 1896.7 | 98.1 | 0.0 |
| B18 | 22.2 | 51 | 1822.7 | 1724.9 | 0.0 | 416.7 | 54.2 | 0.0 |
| B18 | 7.4 | 52 | 38.7 | 40.4 | 0.0 | 50.4 | 6.2 | 0.0 |
| B18 | 2.4 | 53 | 5.7 | 36.8 | 0.0 | 36.4 | 31.1 | 0.0 |
| B18 | 0.8 | 54 | 4.4 | 30.2 | 0.0 | 31.2 | 31.1 | 0.0 |
| B18 | 0.27 | 55 | 5.1 | 29.5 | 0.0 | 22.9 | 0.0 | 0.0 |
| B18 | 0 | 56 | 5.9 | 31.0 | 0.0 | 27.4 | 6.2 | 0.0 |
| B20 | 200 | 57 | 22.0 | 51.5 | 0.0 | 21.3 | 0.0 | 0.0 |
| B20 | 66.6 | 58 | 81.3 | 24.9 | 0.0 | 67.4 | 6.2 | 0.0 |
| B20 | 22.2 | 59 | 95.8 | 36.3 | 0.0 | 147.0 | 31.1 | 0.0 |
| B20 | 7.4 | 60 | 28.0 | 30.2 | 0.0 | 59.8 | 6.2 | 0.0 |
| B20 | 2.4 | 61 | 11.8 | 35.8 | 0.0 | 36.8 | 6.2 | 0.0 |
| B20 | 0.8 | 62 | 3.8 | 33.5 | 0.0 | 27.1 | 31.1 | 0.0 |
| B20 | 0.27 | 63 | 3.3 | 31.8 | 0.0 | 30.1 | 6.2 | 0.0 |
| B20 | 0 | 64 | 9.9 | 39.1 | 0.0 | 37.5 | 6.2 | 0.0 |
| B28 | 200 | 65 | 152.9 | 91.3 | 0.0 | 191.9 | 6.2 | 0.0 |
| B28 | 66.6 | 66 | 188.4 | 194.6 | 0.0 | 145.2 | 54.2 | 0.0 |
| B28 | 22.2 | 67 | 286.4 | 653.7 | 0.0 | 155.1 | 31.1 | 0.0 |
| B28 | 7.4 | 68 | 33.7 | 56.7 | 0.0 | 53.3 | 6.2 | 0.0 |
| B28 | 2.4 | 69 | 12.3 | 29.5 | 0.0 | 33.8 | 54.2 | 0.0 |
| B28 | 0.8 | 70 | 4.6 | 21.7 | 0.0 | 24.0 | 6.2 | 0.0 |
| B28 | 0.27 | 71 | 5.4 | 32.3 | 0.0 | 34.9 | 6.2 | 0.0 |
| B28 | 0 | 72 | 6.2 | 32.3 | 0.0 | 30.8 | 0.0 | 0.0 |
| B30 | 200 | 73 | 27536.4 | 89058.0 | 1.9 | | 119.4 | 0.5 |
| B30 | 66.6 | 74 | 64.7 | 68.0 | 0.0 | 71.7 | 31.1 | 0.0 |
| B30 | 22.2 | 75 | 32.0 | 37.3 | 0.0 | 64.9 | 31.1 | 0.0 |
| B30 | 7.4 | 76 | 13.1 | 28.2 | 0.0 | 48.9 | 6.2 | 0.0 |
| B30 | 2.4 | 77 | 5.1 | 30.0 | 0.0 | 28.2 | 6.2 | 0.0 |
| B30 | 0.8 | 78 | 3.1 | 22.2 | 0.0 | 24.8 | 6.2 | 0.0 |
| B30 | 0.27 | 79 | 2.6 | 21.4 | 0.0 | 19.4 | 6.2 | 0.0 |
| B30 | 0 | 80 | 6.7 | 27.0 | 0.0 | 24.4 | 6.2 | 0.0 |
| B32 | 200 | 81 | 6.2 | 24.4 | 0.0 | 78.1 | 31.1 | 0.0 |
| B32 | 66.6 | 82 | 2.1 | 18.4 | 0.0 | 37.9 | 6.2 | 0.0 |
| B32 | 22.2 | 83 | 15.9 | 51.2 | 0.0 | 64.5 | 31.1 | 0.0 |
| B32 | 7.4 | 84 | 4.6 | 32.3 | 0.0 | 48.2 | 6.2 | 0.0 |
| B32 | 2.4 | 85 | 3.6 | 31.8 | 0.0 | 35.7 | 6.2 | 0.0 |
| B32 | 0.8 | 86 | 3.6 | 28.2 | 0.0 | 26.3 | 6.2 | 0.0 |
| B32 | 0.27 | 87 | 0.9 | 25.2 | 0.0 | 19.4 | 6.2 | 0.0 |
| B32 | 0 | 88 | 3.6 | 24.9 | 0.0 | 24.0 | 6.2 | 0.0 |
| B34 | 200 | 1 | 7.88 | 83.25 | 0.00 | 188.29 | 0.00 | 0.00 |
| B34 | 66.6 | 2 | 7.21 | 60.71 | 0.00 | 97.57 | 0.00 | 0.00 |
| B34 | 22.2 | 3 | 3.27 | 45.21 | 0.00 | 70.74 | 0.00 | 0.00 |
| B34 | 7.4 | 4 | 4.85 | 38.96 | 0.00 | 49.57 | 0.00 | 0.00 |
| B34 | 2.4 | 5 | 5.27 | 38.37 | 0.00 | 46.20 | 0.00 | 0.00 |
| B34 | 0.8 | 6 | 5.69 | 36.03 | 0.00 | 33.17 | 0.00 | 0.00 |
| B34 | 0.27 | 7 | 5.48 | 39.84 | 0.00 | 28.15 | 0.00 | 0.00 |
| B34 | 0 | 8 | 4.05 | 18.93 | 0.00 | 14.44 | 0.00 | 0.00 |
| B36 | 200 | 9 | 5.69 | 56.92 | 0.00 | 196.50 | 0.00 | 0.00 |
| B36 | 66.6 | 10 | 4.45 | 52.86 | 0.00 | 137.85 | 0.00 | 0.00 |
| B36 | 22.2 | 11 | 4.05 | 47.33 | 0.00 | 82.64 | 0.00 | 0.00 |
| B36 | 7.4 | 12 | 4.05 | 48.86 | 0.00 | 76.69 | 0.00 | 0.00 |
| B36 | 2.4 | 13 | 4.25 | 40.73 | 0.00 | 48.73 | 0.00 | 0.00 |
| B36 | 0.8 | 14 | 2.00 | 21.55 | 0.00 | 19.41 | 0.00 | 0.00 |
| B36 | 0.27 | 15 | 3.85 | 36.33 | 0.00 | 31.49 | 0.00 | 0.00 |
| B36 | 0 | 16 | 4.05 | 16.87 | 0.00 | 11.15 | 0.00 | 0.00 |
| B38 | 200 | 17 | 215.43 | 1662.02 | 0.00 | 606.30 | 1.72 | 0.00 |
| B38 | 66.6 | 18 | 22.14 | 213.11 | 0.00 | 149.46 | 0.00 | 0.00 |
| B38 | 22.2 | 19 | 12.64 | 79.58 | 0.00 | 140.43 | 0.00 | 0.00 |
| B38 | 7.4 | 20 | 9.97 | 99.60 | 0.00 | 161.95 | 0.00 | 0.00 |
| B38 | 2.4 | 21 | 4.85 | 51.93 | 0.00 | 75.41 | 0.00 | 0.00 |
| B38 | 0.8 | 22 | 1.83 | 27.52 | 0.00 | 25.65 | 0.00 | 0.00 |
| B38 | 0.27 | 23 | 5.90 | 52.86 | 0.00 | 63.53 | 26.90 | 0.00 |
| B38 | 0 | 24 | 3.46 | 20.23 | 0.00 | 18.58 | 26.90 | 0.00 |
| B40 | 200 | 25 | 56.42 | 45.21 | 0.00 | 92.45 | 0.00 | 0.00 |
| B40 | 66.6 | 26 | 14.65 | 84.93 | 0.00 | 106.12 | 0.00 | 0.00 |
| B40 | 22.2 | 27 | 15.17 | 180.82 | 0.00 | 305.15 | 0.00 | 0.00 |
| B40 | 7.4 | 28 | 20.76 | 250.73 | 0.00 | 360.68 | 0.00 | 0.00 |
| B40 | 2.4 | 29 | 28.70 | 219.83 | 0.00 | 254.62 | 0.00 | 0.00 |
| B40 | 0.8 | 30 | 5.06 | 69.38 | 0.00 | 104.84 | 26.90 | 0.00 |
| B40 | 0.27 | 31 | 4.85 | 81.24 | 0.00 | 117.68 | 0.00 | 0.00 |
| B40 | 0 | 32 | 5.27 | 31.16 | 0.00 | 24.40 | 0.00 | 0.00 |

Figure 3C

| | | | | | | | |
|---|---|---|---|---|---|---|---|
| B42 | 200 | 33 | 6.33 | 67.44 | 0.00 | 184.40 | 0.00 | 0.00 |
| B42 | 66.6 | 34 | 21.58 | 90.68 | 0.00 | 240.28 | 1.72 | 0.00 |
| B42 | 22.2 | 35 | 29.29 | 225.80 | 0.00 | 380.85 | 0.00 | 0.00 |
| B42 | 7.4 | 36 | 10.68 | 133.70 | 0.00 | 323.49 | 26.90 | 0.00 |
| B42 | 2.4 | 37 | 10.92 | 117.50 | 0.00 | 249.84 | 1.72 | 0.00 |
| B42 | 0.8 | 38 | 2.17 | 47.94 | 0.00 | 62.25 | 0.00 | 0.00 |
| B42 | 0.27 | 39 | 8.79 | 106.56 | 0.00 | 186.99 | 26.90 | 0.00 |
| B42 | 0 | 40 | 7.21 | 41.62 | 0.00 | 28.15 | 0.00 | 0.00 |
| B44 | 200 | 41 | 17.79 | 71.01 | 0.00 | 103.55 | 0.00 | 0.00 |
| B44 | 66.6 | 42 | 7.43 | 41.92 | 0.00 | 75.84 | 0.00 | 0.00 |
| B44 | 22.2 | 43 | 121.66 | 307.32 | 0.00 | 256.36 | 0.00 | 0.00 |
| B44 | 7.4 | 44 | 7.88 | 81.58 | 0.00 | 164.11 | 0.00 | 0.00 |
| B44 | 2.4 | 45 | 10.68 | 101.33 | 0.00 | 236.81 | 26.90 | 0.00 |
| B44 | 0.8 | 46 | 4.65 | 74.28 | 0.00 | 176.19 | 0.00 | 0.00 |
| B44 | 0.27 | 47 | 5.06 | 63.26 | 0.00 | 138.28 | 0.00 | 0.00 |
| B44 | 0 | 48 | 7.65 | 33.73 | 0.00 | 31.91 | 1.72 | 0.00 |
| B46 | 200 | 49 | 17.25 | 85.60 | 0.00 | 178.35 | 0.00 | 0.00 |
| B46 | 66.6 | 50 | 25.23 | 105.51 | 0.00 | 212.95 | 26.90 | 0.00 |
| B46 | 22.2 | 51 | 21.86 | 82.24 | 0.00 | 153.77 | 1.72 | 0.00 |
| B46 | 7.4 | 52 | 3.65 | 86.28 | 0.00 | 240.72 | 1.72 | 0.00 |
| B46 | 2.4 | 53 | 4.65 | 70.03 | 0.00 | 150.75 | 0.00 | 0.00 |
| B46 | 0.8 | 54 | 3.27 | 46.42 | 0.00 | 98.85 | 0.00 | 0.00 |
| B46 | 0.27 | 55 | 4.45 | 47.64 | 0.00 | 101.42 | 26.90 | 0.00 |
| B46 | 0 | 56 | 3.27 | 19.97 | 0.00 | 19.41 | 0.00 | 0.00 |
| sTDCM | 200 | 57 | 0.00 | 0.00 | 0.00 | 1603.11 | 1.72 | 0.00 |
| sTDCM | 66.6 | 58 | 0.00 | 0.00 | 0.00 | 2495.11 | 73.33 | 1.10 |
| sTDCM | 22.2 | 59 | 0.00 | 0.00 | 0.00 | 1579.01 | 26.90 | 0.00 |
| sTDCM | 7.4 | 60 | 7527.77 | 0.00 | 0.00 | 1298.83 | 26.90 | 3.02 |
| sTDCM | 2.4 | 61 | 2050.40 | 0.00 | 0.00 | 906.69 | 73.33 | 0.00 |
| sTDCM | 0.8 | 62 | 444.61 | 1868.46 | 0.00 | 214.69 | 0.00 | 0.00 |
| sTDCM | 0.27 | 63 | 4.65 | 16.62 | 0.00 | 19.82 | 26.90 | 0.00 |
| sTDCM | 0 | 64 | 3.85 | 18.67 | 0.00 | 16.09 | 0.00 | 0.00 |
| TDM | 200 | 65 | 12.88 | 90.00 | 0.00 | 445.03 | 0.00 | 0.00 |
| TDM | 66.6 | 66 | 6.33 | 30.88 | 0.00 | 41.99 | 0.00 | 0.00 |
| TDM | 22.2 | 67 | 3.27 | 26.97 | 0.00 | 35.27 | 0.00 | 0.00 |
| TDM | 7.4 | 68 | 6.11 | 40.14 | 0.00 | 49.99 | 0.00 | 0.00 |
| TDM | 2.4 | 69 | 4.65 | 36.33 | 0.00 | 53.79 | 0.00 | 0.00 |
| TDM | 0.8 | 70 | 5.69 | 41.92 | 0.00 | 58.02 | 0.00 | 0.00 |
| TDM | 0.27 | 71 | 5.90 | 89.66 | 0.00 | 156.78 | 1.72 | 0.00 |
| TDM | 0 | 72 | 3.08 | 15.61 | 0.00 | 12.79 | 0.00 | 0.00 |
| TDB | 200 | 73 | 57.76 | 266.22 | 0.00 | 316.50 | 0.00 | 0.00 |
| TDB | 66.6 | 74 | 12.39 | 104.12 | 0.00 | 230.73 | 0.00 | 0.00 |
| TDB | 22.2 | 75 | 105.13 | 543.62 | 0.00 | 279.43 | 0.00 | 0.00 |
| TDB | 7.4 | 76 | 4.05 | 57.86 | 0.00 | 112.54 | 0.00 | 0.00 |
| TDB | 2.4 | 77 | 2.90 | 46.12 | 0.00 | 81.79 | 0.00 | 0.00 |
| TDB | 0.8 | 78 | 4.05 | 47.33 | 0.00 | 91.17 | 0.00 | 0.00 |
| TDB | 0.27 | 79 | 2.71 | 43.41 | 0.00 | 68.61 | 0.00 | 0.00 |
| TDB | 0 | 80 | 5.06 | 19.19 | 0.00 | 19.82 | 0.00 | 0.00 |
| MMG | 200 | 81 | 4771.13 | 0.00 | 0.00 | 848.89 | 1.72 | 0.00 |
| MMG | 66.6 | 82 | 2993.52 | 0.00 | 0.00 | 1022.86 | 117.97 | 0.00 |
| MMG | 22.2 | 83 | 5065.18 | 0.00 | 0.00 | 1222.82 | 1.72 | 0.00 |
| MMG | 7.4 | 84 | 428.50 | 1741.97 | 0.00 | 163.25 | 0.00 | 0.00 |
| MMG | 2.4 | 85 | 30.17 | 83.58 | 0.00 | 32.75 | 26.90 | 0.00 |
| MMG | 0.8 | 86 | 5.06 | 22.35 | 0.00 | 12.79 | 0.00 | 0.00 |
| MMG | 0.27 | 87 | 4.65 | 28.63 | 0.00 | 16.92 | 0.00 | 0.00 |
| MMG | 0 | 88 | 2.17 | 17.13 | 0.00 | 13.20 | 0.00 | 0.00 |

SEQUENCE LISTING

```
<160> NUMBER OF SEQ ID NOS: 4

<210> SEQ ID NO 1
<211> LENGTH: 391
<212> TYPE: PRT
<213> ORGANISM: Mycobacterium tuberculosis

<400> SEQUENCE: 1

Met Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Ala Gln Met Trp
            20                  25                  30

Asp Ser Val Ala Ser Asp Leu Phe Ser Ala Ala Ser Ala Phe Gln Ser
        35                  40                  45

Val Val Trp Gly Leu Thr Val Gly Ser Trp Ile Gly Ser Ser Ala Gly
    50                  55                  60

Leu Met Val Ala Ala Ala Ser Pro Tyr Val Ala Trp Met Ser Val Thr
65                  70                  75                  80
```

```
Ala Gly Gln Ala Glu Leu Thr Ala Ala Gln Val Arg Val Ala Ala
                85                  90                  95

Ala Tyr Glu Thr Ala Tyr Gly Leu Thr Val Pro Pro Val Ile Ala
            100                 105                 110

Glu Asn Arg Ala Glu Leu Met Ile Leu Ile Ala Thr Asn Leu Leu Gly
            115                 120                 125

Gln Asn Thr Pro Ala Ile Ala Val Asn Glu Ala Glu Tyr Gly Glu Met
            130                 135                 140

Trp Ala Gln Asp Ala Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                165                 170                 175

Ser Ala Gly Gly Leu Leu Glu Gln Ala Ala Val Glu Glu Ala Ser
            180                 185                 190

Asp Thr Ala Ala Ala Asn Gln Leu Met Asn Asn Val Pro Gln Ala Leu
            195                 200                 205

Gln Gln Leu Ala Gln Pro Thr Gln Gly Thr Thr Pro Ser Ser Lys Leu
            210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
                260                 265                 270

Ala Ala Ala Gln Ala Val Gln Thr Ala Ala Gln Asn Gly Val Arg Ala
            275                 280                 285

Met Ser Ser Leu Gly Ser Ser Leu Gly Ser Ser Gly Leu Gly Gly Gly
            290                 295                 300

Val Ala Ala Asn Leu Gly Arg Ala Ala Ser Val Gly Ser Leu Ser Val
305                 310                 315                 320

Pro Gln Ala Trp Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly
                340                 345                 350

Gln Met Leu Gly Gly Leu Pro Val Gly Gln Met Gly Ala Arg Ala Gly
            355                 360                 365

Gly Gly Leu Ser Gly Val Leu Arg Val Pro Pro Arg Pro Tyr Val Met
            370                 375                 380

Pro His Ser Pro Ala Ala Gly
385                 390

<210> SEQ ID NO 2
<211> LENGTH: 323
<212> TYPE: PRT
<213> ORGANISM: Mycobacterium tuberculosis

<400> SEQUENCE: 2

Ala Pro Pro Ala Leu Ser Gln Asp Arg Phe Ala Asp Phe Pro Ala Leu
1               5                   10                  15

Pro Leu Asp Pro Ser Ala Met Val Ala Gln Val Gly Pro Gln Val Val
                20                  25                  30

Asn Ile Asn Thr Lys Leu Gly Tyr Asn Asn Ala Val Gly Ala Gly Thr
                35                  40                  45

Gly Ile Val Ile Asp Pro Asn Gly Val Val Leu Thr Asn Asn His Val
```

```
        50                  55                  60
Ile Ala Gly Ala Thr Asp Ile Asn Ala Phe Ser Val Gly Ser Gly Gln
 65                  70                  75                  80

Thr Tyr Gly Val Asp Val Gly Tyr Asp Arg Thr Gln Asp Val Ala
                 85                  90                  95

Val Leu Gln Leu Arg Gly Ala Gly Leu Pro Ser Ala Ala Ile Gly
                100                 105                 110

Gly Gly Val Ala Val Gly Glu Pro Val Ala Met Gly Asn Ser Gly
                115                 120                 125

Gly Gln Gly Gly Thr Pro Arg Ala Val Pro Gly Arg Val Val Ala Leu
                130                 135                 140

Gly Gln Thr Val Gln Ala Ser Asp Ser Leu Thr Gly Ala Glu Glu Thr
145                 150                 155                 160

Leu Asn Gly Leu Ile Gln Phe Asp Ala Ala Ile Gln Pro Gly Asp Ser
                165                 170                 175

Gly Gly Pro Val Val Asn Gly Leu Gly Gln Val Val Gly Met Asn Thr
                180                 185                 190

Ala Ala Ser Asp Asn Phe Gln Leu Ser Gln Gly Gly Gln Gly Phe Ala
                195                 200                 205

Ile Pro Ile Gly Gln Ala Met Ala Ile Ala Gly Gln Ile Arg Ser Gly
                210                 215                 220

Gly Gly Ser Pro Thr Val His Ile Gly Pro Thr Ala Phe Leu Gly Leu
225                 230                 235                 240

Gly Val Val Asp Asn Asn Gly Asn Gly Ala Arg Val Gln Arg Val Val
                245                 250                 255

Gly Ser Ala Pro Ala Ala Ser Leu Gly Ile Ser Thr Gly Asp Val Ile
                260                 265                 270

Thr Ala Val Asp Gly Ala Pro Ile Asn Ser Ala Thr Ala Met Ala Asp
                275                 280                 285

Ala Leu Asn Gly His His Pro Gly Asp Val Ile Ser Val Thr Trp Gln
                290                 295                 300

Thr Lys Ser Gly Gly Thr Arg Thr Gly Asn Val Thr Leu Ala Glu Gly
305                 310                 315                 320

Pro Pro Ala

<210> SEQ ID NO 3
<211> LENGTH: 723
<212> TYPE: PRT
<213> ORGANISM: Artificial
<220> FEATURE:
<223> OTHER INFORMATION: M72

<400> SEQUENCE: 3

Met Thr Ala Ala Ser Asp Asn Phe Gln Leu Ser Gln Gly Gly Gln Gly
 1               5                  10                  15

Phe Ala Ile Pro Ile Gly Gln Ala Met Ala Ile Ala Gly Gln Ile Arg
                20                  25                  30

Ser Gly Gly Gly Ser Pro Thr Val His Ile Gly Pro Thr Ala Phe Leu
            35                  40                  45

Gly Leu Gly Val Val Asp Asn Asn Gly Asn Gly Ala Arg Val Gln Arg
        50                  55                  60

Val Val Gly Ser Ala Pro Ala Ala Ser Leu Gly Ile Ser Thr Gly Asp
 65                  70                  75                  80

Val Ile Thr Ala Val Asp Gly Ala Pro Ile Asn Ser Ala Thr Ala Met
                85                  90                  95
```

-continued

```
Ala Asp Ala Leu Asn Gly His His Pro Gly Asp Val Ile Ser Val Thr
            100                 105                 110

Trp Gln Thr Lys Ser Gly Gly Thr Arg Thr Gly Asn Val Thr Leu Ala
            115                 120                 125

Glu Gly Pro Pro Ala Glu Phe Met Val Asp Phe Gly Ala Leu Pro Pro
            130                 135                 140

Glu Ile Asn Ser Ala Arg Met Tyr Ala Gly Pro Gly Ser Ala Ser Leu
145                 150                 155                 160

Val Ala Ala Ala Gln Met Trp Asp Ser Val Ala Ser Asp Leu Phe Ser
                165                 170                 175

Ala Ala Ser Ala Phe Gln Ser Val Val Trp Gly Leu Thr Val Gly Ser
            180                 185                 190

Trp Ile Gly Ser Ser Ala Gly Leu Met Val Ala Ala Ser Pro Tyr
            195                 200                 205

Val Ala Trp Met Ser Val Thr Ala Gly Gln Ala Glu Leu Thr Ala Ala
            210                 215                 220

Gln Val Arg Val Ala Ala Ala Tyr Glu Thr Ala Tyr Gly Leu Thr
225                 230                 235                 240

Val Pro Pro Pro Val Ile Ala Glu Asn Arg Ala Glu Leu Met Ile Leu
            245                 250                 255

Ile Ala Thr Asn Leu Leu Gly Gln Asn Thr Pro Ala Ile Ala Val Asn
            260                 265                 270

Glu Ala Glu Tyr Gly Glu Met Trp Ala Gln Asp Ala Ala Ala Met Phe
            275                 280                 285

Gly Tyr Ala Ala Ala Thr Ala Thr Ala Thr Ala Leu Leu Pro Phe
            290                 295                 300

Glu Glu Ala Pro Glu Met Thr Ser Ala Gly Gly Leu Leu Glu Gln Ala
305                 310                 315                 320

Ala Ala Val Glu Glu Ala Ser Asp Thr Ala Ala Ala Asn Gln Leu Met
                325                 330                 335

Asn Asn Val Pro Gln Ala Leu Gln Gln Leu Ala Gln Pro Thr Gln Gly
            340                 345                 350

Thr Thr Pro Ser Ser Lys Leu Gly Gly Leu Trp Lys Thr Val Ser Pro
            355                 360                 365

His Arg Ser Pro Ile Ser Asn Met Val Ser Met Ala Asn Asn His Met
            370                 375                 380

Ser Met Thr Asn Ser Gly Val Ser Met Thr Asn Thr Leu Ser Ser Met
385                 390                 395                 400

Leu Lys Gly Phe Ala Pro Ala Ala Ala Gln Ala Val Gln Thr Ala
                405                 410                 415

Ala Gln Asn Gly Val Arg Ala Met Ser Ser Leu Gly Ser Ser Leu Gly
            420                 425                 430

Ser Ser Gly Leu Gly Gly Gly Val Ala Ala Asn Leu Gly Arg Ala Ala
            435                 440                 445

Ser Val Gly Ser Leu Ser Val Pro Gln Ala Trp Ala Ala Ala Asn Gln
            450                 455                 460

Ala Val Thr Pro Ala Ala Arg Ala Leu Pro Leu Thr Ser Leu Thr Ser
465                 470                 475                 480

Ala Ala Glu Arg Gly Pro Gly Gln Met Leu Gly Gly Leu Pro Val Gly
                485                 490                 495

Gln Met Gly Ala Arg Ala Gly Gly Gly Leu Ser Gly Val Leu Arg Val
            500                 505                 510
```

```
Pro Pro Arg Pro Tyr Val Met Pro His Ser Pro Ala Ala Gly Asp Ile
            515                 520                 525

Ala Pro Pro Ala Leu Ser Gln Asp Arg Phe Ala Asp Phe Pro Ala Leu
    530                 535                 540

Pro Leu Asp Pro Ser Ala Met Val Ala Gln Val Gly Pro Gln Val Val
545                 550                 555                 560

Asn Ile Asn Thr Lys Leu Gly Tyr Asn Asn Ala Val Gly Ala Gly Thr
                565                 570                 575

Gly Ile Val Ile Asp Pro Asn Gly Val Val Leu Thr Asn Asn His Val
                580                 585                 590

Ile Ala Gly Ala Thr Asp Ile Asn Ala Phe Ser Val Gly Ser Gly Gln
            595                 600                 605

Thr Tyr Gly Val Asp Val Val Gly Tyr Asp Arg Thr Gln Asp Val Ala
            610                 615                 620

Val Leu Gln Leu Arg Gly Ala Gly Gly Leu Pro Ser Ala Ala Ile Gly
625                 630                 635                 640

Gly Gly Val Ala Val Gly Glu Pro Val Val Ala Met Gly Asn Ser Gly
                645                 650                 655

Gly Gln Gly Gly Thr Pro Arg Ala Val Pro Gly Arg Val Val Ala Leu
                660                 665                 670

Gly Gln Thr Val Gln Ala Ser Asp Ser Leu Thr Gly Ala Glu Glu Thr
            675                 680                 685

Leu Asn Gly Leu Ile Gln Phe Asp Ala Ala Ile Gln Pro Gly Asp Ala
            690                 695                 700

Gly Gly Pro Val Val Asn Gly Leu Gly Gln Val Val Gly Met Asn Thr
705                 710                 715                 720

Ala Ala Ser

<210> SEQ ID NO 4
<211> LENGTH: 725
<212> TYPE: PRT
<213> ORGANISM: Artificial
<220> FEATURE:
<223> OTHER INFORMATION: M72-2His

<400> SEQUENCE: 4

Met His His Thr Ala Ala Ser Asp Asn Phe Gln Leu Ser Gln Gly Gly
1               5                   10                  15

Gln Gly Phe Ala Ile Pro Ile Gly Gln Ala Met Ala Ile Ala Gly Gln
                20                  25                  30

Ile Arg Ser Gly Gly Gly Ser Pro Thr Val His Ile Gly Pro Thr Ala
            35                  40                  45

Phe Leu Gly Leu Gly Val Val Asp Asn Asn Gly Asn Gly Ala Arg Val
    50                  55                  60

Gln Arg Val Val Gly Ser Ala Pro Ala Ala Ser Leu Gly Ile Ser Thr
65                  70                  75                  80

Gly Asp Val Ile Thr Ala Val Asp Gly Ala Pro Ile Asn Ser Ala Thr
                85                  90                  95

Ala Met Ala Asp Ala Leu Asn Gly His His Pro Gly Asp Val Ile Ser
                100                 105                 110

Val Thr Trp Gln Thr Lys Ser Gly Gly Thr Arg Thr Gly Asn Val Thr
            115                 120                 125

Leu Ala Glu Gly Pro Pro Ala Glu Phe Met Val Asp Phe Gly Ala Leu
    130                 135                 140

Pro Pro Glu Ile Asn Ser Ala Arg Met Tyr Ala Gly Pro Gly Ser Ala
```

-continued

```
            145                 150                 155                 160
        Ser Leu Val Ala Ala Ala Gln Met Trp Asp Ser Val Ala Ser Asp Leu
                        165                 170                 175
        Phe Ser Ala Ala Ser Ala Phe Gln Ser Val Val Trp Gly Leu Thr Val
                        180                 185                 190
        Gly Ser Trp Ile Gly Ser Ser Ala Gly Leu Met Val Ala Ala Ala Ser
                        195                 200                 205
        Pro Tyr Val Ala Trp Met Ser Val Thr Ala Gly Gln Ala Glu Leu Thr
                        210                 215                 220
        Ala Ala Gln Val Arg Val Ala Ala Ala Tyr Glu Thr Ala Tyr Gly
        225                 230                 235                 240
        Leu Thr Val Pro Pro Val Ile Ala Glu Asn Arg Ala Glu Leu Met
                            245                 250                 255
        Ile Leu Ile Ala Thr Asn Leu Gly Gln Asn Thr Pro Ala Ile Ala
                        260                 265                 270
        Val Asn Glu Ala Glu Tyr Gly Glu Met Trp Ala Gln Asp Ala Ala
                        275                 280                 285
        Met Phe Gly Tyr Ala Ala Ala Thr Ala Thr Ala Thr Ala Thr Leu Leu
                        290                 295                 300
        Pro Phe Glu Glu Ala Pro Glu Met Thr Ser Ala Gly Gly Leu Leu Glu
        305                 310                 315                 320
        Gln Ala Ala Ala Val Glu Glu Ala Ser Asp Thr Ala Ala Asn Gln
                        325                 330                 335
        Leu Met Asn Asn Val Pro Gln Ala Leu Gln Gln Leu Ala Gln Pro Thr
                        340                 345                 350
        Gln Gly Thr Thr Pro Ser Ser Lys Leu Gly Gly Leu Trp Lys Thr Val
                        355                 360                 365
        Ser Pro His Arg Ser Pro Ile Ser Asn Met Val Ser Met Ala Asn Asn
                        370                 375                 380
        His Met Ser Met Thr Asn Ser Gly Val Ser Met Thr Asn Thr Leu Ser
        385                 390                 395                 400
        Ser Met Leu Lys Gly Phe Ala Pro Ala Ala Ala Gln Ala Val Gln
                        405                 410                 415
        Thr Ala Ala Gln Asn Gly Val Arg Ala Met Ser Ser Leu Gly Ser Ser
                        420                 425                 430
        Leu Gly Ser Ser Gly Leu Gly Gly Gly Val Ala Ala Asn Leu Gly Arg
                        435                 440                 445
        Ala Ala Ser Val Gly Ser Leu Ser Val Pro Gln Ala Trp Ala Ala Ala
                        450                 455                 460
        Asn Gln Ala Val Thr Pro Ala Ala Arg Ala Leu Pro Leu Thr Ser Leu
        465                 470                 475                 480
        Thr Ser Ala Ala Glu Arg Gly Pro Gly Gln Met Leu Gly Gly Leu Pro
                        485                 490                 495
        Val Gly Gln Met Gly Ala Arg Ala Gly Gly Leu Ser Gly Val Leu
                        500                 505                 510
        Arg Val Pro Pro Arg Pro Tyr Val Met Pro His Ser Pro Ala Ala Gly
                        515                 520                 525
        Asp Ile Ala Pro Pro Ala Leu Ser Gln Asp Arg Phe Ala Asp Phe Pro
                        530                 535                 540
        Ala Leu Pro Leu Asp Pro Ser Ala Met Val Ala Gln Val Gly Pro Gln
        545                 550                 555                 560
        Val Val Asn Ile Asn Thr Lys Leu Gly Tyr Asn Ala Val Gly Ala
                        565                 570                 575
```

```
Gly Thr Gly Ile Val Ile Asp Pro Asn Gly Val Val Leu Thr Asn Asn
            580                 585                 590

His Val Ile Ala Gly Ala Thr Asp Ile Asn Ala Phe Ser Val Gly Ser
            595                 600                 605

Gly Gln Thr Tyr Gly Val Asp Val Val Gly Tyr Asp Arg Thr Gln Asp
            610                 615                 620

Val Ala Val Leu Gln Leu Arg Gly Ala Gly Gly Leu Pro Ser Ala Ala
625                 630                 635                 640

Ile Gly Gly Val Ala Val Gly Glu Pro Val Ala Met Gly Asn
                645                 650                 655

Ser Gly Gly Gln Gly Gly Thr Pro Arg Ala Val Pro Gly Arg Val Val
            660                 665                 670

Ala Leu Gly Gln Thr Val Gln Ala Ser Asp Ser Leu Thr Gly Ala Glu
            675                 680                 685

Glu Thr Leu Asn Gly Leu Ile Gln Phe Asp Ala Ala Ile Gln Pro Gly
            690                 695                 700

Asp Ala Gly Gly Pro Val Val Asn Gly Leu Gly Gln Val Val Gly Met
705                 710                 715                 720

Asn Thr Ala Ala Ser
            725
```

IMMUNIGENIC ALPHA-BRANCHED TREHALOSE-DIESTERS

CROSS REFERENCE TO RELATED APPLICATIONS

This application is the National Phase of PCT International Application No. PCT/EP2019/059385, filed on Apr. 12, 2019, which claims priority under 35 U.S.C. 119(e) to U.S. Provisional Application No. 62/657,078, filed on Apr. 13, 2018, all of which are hereby expressly incorporated by reference into the present application.

GOVERNMENT SUPPORT CLAUSE

This invention was made with United States government support under Contract No. HHSN272201400050C awarded by the National Institutes of Health (NIH). The United States government has certain rights in the invention.

FIELD OF THE INVENTION

The invention relates to novel compounds, the use of compounds in eliciting a pro-Th17 immune response and related aspects. Further provided are methods of production of said compounds.

BACKGROUND OF THE INVENTION

Adjuvants are included in vaccines to improve humoral and cellular immune responses, particularly in the case of poorly immunogenic subunit vaccines. Similar to natural infections by pathogens, adjuvants rely on the activation of the innate immune system to promote long-lasting adaptive immunity. As simultaneous activation of multiple innate immune pathways is a feature of natural infections, adjuvants may combine multiple immunostimulants in order to promote adaptive immune responses to vaccination.

IL-17 (also known as IL-17A) production by T cells is required for protection against some pathogens. It has been demonstrated that IL-17A is produced by a unique subset of T helper cells. T cells can differentiate into IL-17-producing cells in vitro and in vivo independently of Th1 or Th2 cell development thereby establishing Th17 cells as a unique T helper cell lineage. Functionally, Th17 cells play a role in host defence against extracellular pathogens by mediating the recruitment of neutrophils and macrophages to infected tissues. Moreover, it has become evident that aberrant regulation of Th17 cells may play a significant role in the pathogenesis of multiple inflammatory and autoimmune disorders.

Yamamoto et al (2013) discloses alpha-branched trehalose 6,6'-diesters with symmetrical alkyl chains having 8 to 16 atoms in each carbon branch, beta-branched trehalose 6,6'-diesters with symmetrical alkyl chains having 8 to 14 atoms in each carbon branch and gamma-branched trehalose 6,6'-diesters. Certain compounds were shown to induce IL-6 and MIP-1β and to have a prophylactic effect on experimental lung metastasis of B16-F0 melanoma cells. The authors state that a beta-branched derivative with 9 carbon atoms in each branch showed the highest activity, followed by an alpha-branched derivative with 10 carbon atoms in each branch. Gamma-branched trehalose 6,6'-diesters were found to be practically inactive. The authors further state that alpha- or beta-branching is essential for activity and the optimal chain length for the ester moiety is 12 atoms. The chain length of the fatty acid residue was found to significantly affect the immunostimulating activity. The immunostimulating activities disclosed do not include pro-Th17 responses.

Kallerup et al (2015) discloses trehalose 6,6'-diester compounds with linear diarachidate, distearate, dipalmitate, dimyristate and dilaurate ester moieties. A mixed Th1/Th17 based immune response inducing IFN-γ, TNF-α and IL-17a was observed in mice when formulated with dimethyldioctadecylammonium bromide in liposomes.

Huber et al (2016) discloses trehalose 6,6'-diester compounds with linear diarachidate, distearate, dipalmitate and dimyristate ester moieties. The compounds are said to activate macrophages via Mincle signalling independently of MyD88. The stearate diester, when formulated with dimethyldioctadecylammonium bromide in liposomes, was found to produce a Th1/Th17 cell response in mice. The authors suggest that immune activation is independent of chain length for these trehalose 6,6'-diester compounds.

Decout et al (2017) discloses trehalose-6,6'-dimycolate and trehalose-6,6'-dibehenate together with glucose and mannose derivatives, as ligands of the Mincle receptor. Mice immunised with a glucose derivative and dimethyldioctadecylammonium bromide in liposomes were found to provide a Th1 and Th17 immune response. Immunisation with trehalose-6,6'-dibehenate and dimethyldioctadecylammonium bromide in liposomes did not result in a significant increase in IL-2, IFN-gamma or IL-17. The paper states that the precise molecular mechanisms of the glycolipid-Mincle interaction are far from being completely understood.

Khan et al (2011) reports tests of a variety of trehalose 6,6'-diester compounds with linear ester moieties with chains between 4 and 26 carbons in length. The authors found that the shorter chained compounds (04-010) were inactive when tested for cytokine and NO production.

Van der Peet et al (2015) discloses derivatives of glucose mono-corynomycolate and trehalose di-corynomycolate compounds signalling through the Mincle receptor. It is also reported that monoacyl trehalose derivatives with longer chain lengths generally provided greater potency of activation in Mincle reporter assays.

Van der Peet (2016) et al discloses glucose monocorynomycolates signalling through the Mincle receptor.

Foster et al (2018) discloses lipidated brartemicin analogues as Th1-stimulating vaccine adjuvants.

EP2123662 discloses amide-branched trehalose compounds with carbon chains of 10 to 16 exhibiting immunostimulating properties of macrophage activation, neutrophil activation and phagocytosis activation. There is no disclosure of a pro-Th17 response.

U.S. Pat. No. 8,163,713 discloses alpha-branched trehalose 6,6'-diester compounds with various chain lengths, though with a maximum of 6 atoms in some branches. The compounds are identified as having high affinity as antagonists for adenosine A3 receptors. Antagonists for adenosine A3 receptors are disclosed as being useful as anti-asthmatic drugs, therapeutic agents for chronic obstructive pulmonary disease, brain protection medicine and anti-phlogistics. The use of compounds as adjuvants is not described.

U.S. Pat. No. 8,741,871 discloses trehalose 6,6'-diesters, including exemplification of symmetrical alkyl chains having 8 to 16 atoms in each carbon branch. The compounds are stated to exhibit excellent anti-bacterial activity on infectious diseases caused by pathogenic bacteria and that they have a high activating effect on macrophages and neutrophils. The use of compounds as adjuvants is not described.

There remains a need for the identification of novel immunostimulatory compounds, particularly those which may be of use as adjuvants and/or in the stimulation of pro-Th17 immune responses, especially for human use. It has now been discovered by the present inventors that certain α-branched trehalose compounds surprisingly elicit a potent pro-Th17 immune response. Furthermore, certain of these α-branched trehalose compounds have not previously been described in the art.

SUMMARY OF THE INVENTION

The present invention provides a compound of formula (Ia):

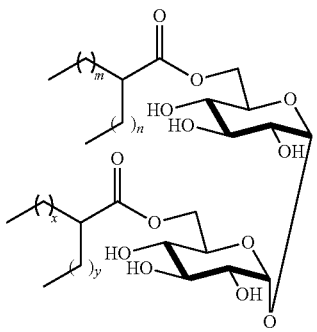

(Ia)

wherein m is 5, 6 or 7; n is 5, 6 or 7; x is 5, 6 or 7; y is 5, 6 or 7; provided that m+n is 11, 12 or 13.

There is also provided a compound of formula (I):

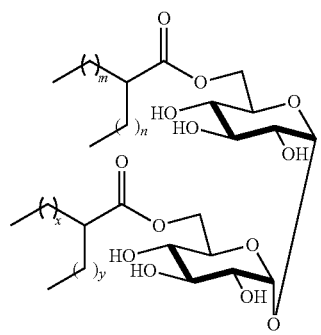

(I)

wherein m is an integer between 3 and 13; n is an integer between 3 and 13; x is an integer between 3 and 13; y is an integer between 3 and 13;

for use in eliciting a pro-Th17 immune response.

Additionally provided is a compound of formula (I):

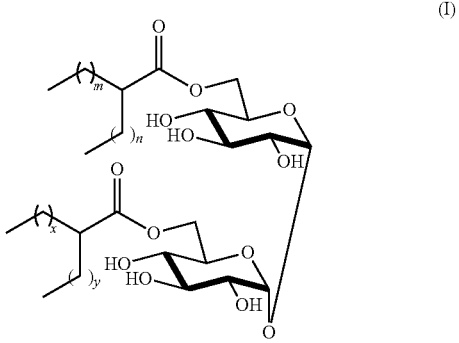

(I)

wherein m is an integer between 3 and 13; n is an integer between 3 and 13; x is an integer between 3 and 13; y is an integer between 3 and 13;

for use as an adjuvant.

Also provided is the use of a compound of formula (I):

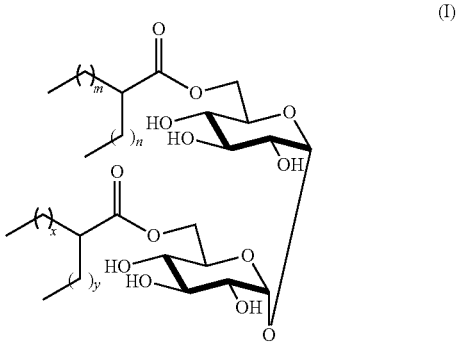

(I)

wherein m is an integer between 3 and 13; n is an integer between 3 and 13; x is an integer between 3 and 13; y is an integer between 3 and 13;

in the manufacture of a medicament for eliciting a pro-Th17 immune response.

There is also provided the use of a compound of formula (I):

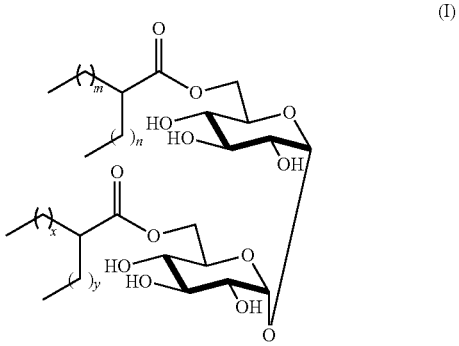

(I)

wherein m is an integer between 3 and 13; n is an integer between 3 and 13; x is an integer between 3 and 13; y is an integer between 3 and 13;

in the manufacture of an adjuvant.

The present invention provides a method for eliciting a pro-Th17 immune response in a subject, said method comprising the step of administering a compound of formula (I):

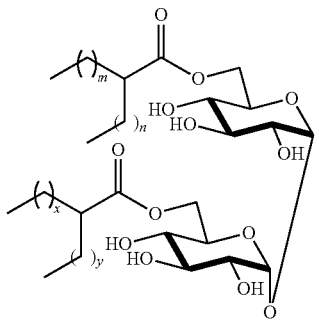

wherein m is an integer between 3 and 13; n is an integer between 3 and 13; x is an integer between 3 and 13; y is an integer between 3 and 13;
to the subject.

Also provided is a method for adjuvanting an immune response in a subject, said method comprising the step of administering a compound of formula (I):

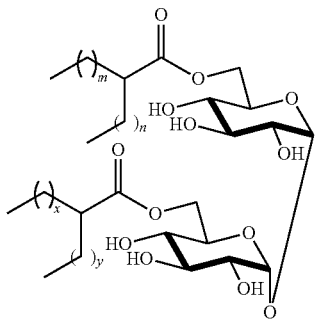

wherein m is an integer between 3 and 13; n is an integer between 3 and 13; x is an integer between 3 and 13; y is an integer between 3 and 13;
to the subject.

A further aspect of the invention is a compound of formula (I)

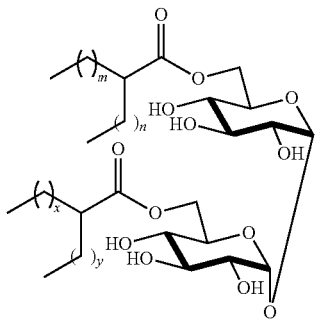

wherein m is an integer between 3 and 13; n is an integer between 3 and 13; x is an integer between 3 and 13; y is an integer between 3 and 13;
for use as a human medicament.

A compound of formula (I) or (Ia) may be provided in the form of a salt and/or solvate thereof and/or prodrug thereof. Suitably, the compound of formula (I) is provided in the form of a pharmaceutically acceptable salt and/or solvate thereof and/or prodrug thereof. In one embodiment, the compound of formula (I) is provided in the form of a pharmaceutically acceptable salt and/or solvate, in particular the compound of formula (I) is provided in the form of a pharmaceutically acceptable salt.

DESCRIPTION OF THE FIGURES

FIG. 3A-C: Tabulated data for FIG. 2.

DESCRIPTION OF SEQUENCE IDENTIFIERS

Figure 1:
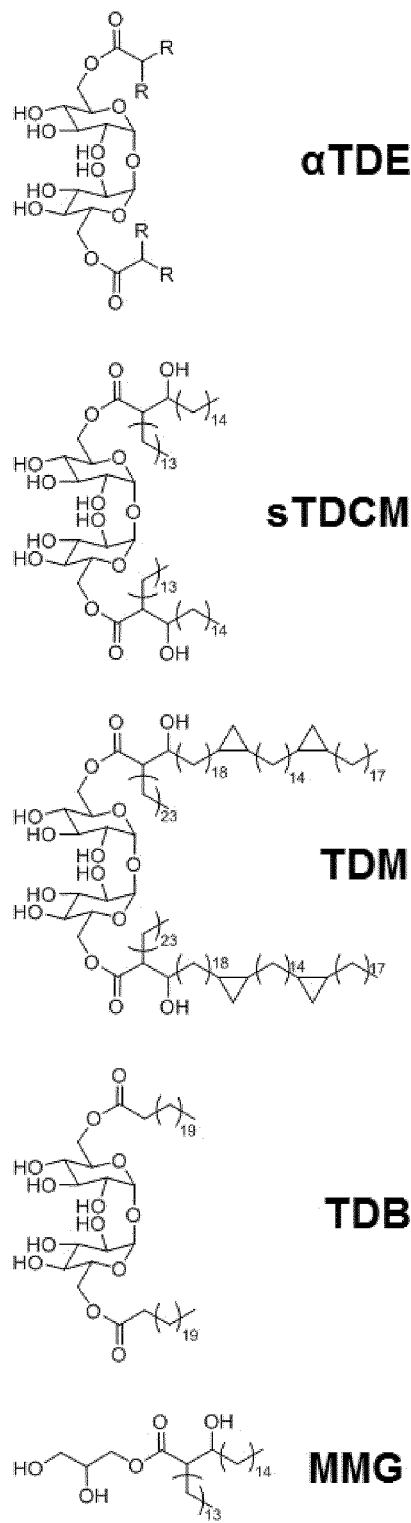
FIG. 1: Overview of alpha branched trehalose diester (TDE) compounds and related structures.

SEQ ID No. 1: *M. tuberculosis* H37Rv strain Rv1196 polypeptide sequence

SEQ ID No. 2: *M. tuberculosis* H37Rv strain Rv0125 polypeptide sequence

SEQ ID No. 3: M72 fusion polypeptide sequence

SEQ ID No. 4: M72-2his fusion polypeptide sequence

DETAILED DESCRIPTION OF THE INVENTION

There is provided a compound of formula (Ia):

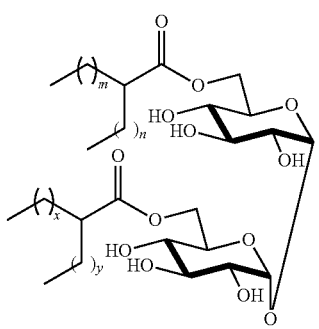

wherein m is 5, 6 or 7; n is 5, 6 or 7; x is 5, 6 or 7; y is 5, 6 or 7; provided that m+n is 11, 12 or 13;

or a pharmaceutically acceptable salt and/or solvate and/or prodrug thereof.

There is also provided a compound of formula (I):

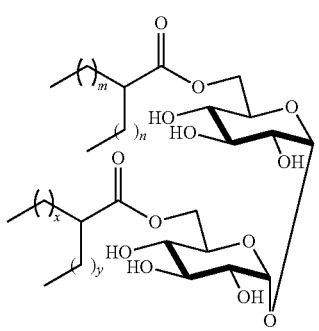

(I)

wherein m is an integer between 3 and 13; n is an integer between 3 and 13; x is an integer between 3 and 13; y is an integer between 3 and 13;

or a pharmaceutically acceptable salt and/or solvate and/or prodrug thereof for use in eliciting a pro-Th17 immune response.

Additionally provided a compound of formula (I):

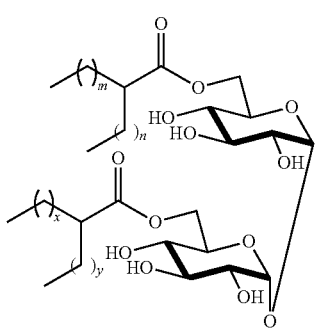

(I)

wherein m is an integer between 3 and 13; n is an integer between 3 and 13; x is an integer between 3 and 13; y is an integer between 3 and 13;

or a pharmaceutically acceptable salt and/or solvate and/or prodrug thereof, for use as an adjuvant.

Also provided is the use of a compound of formula (I):

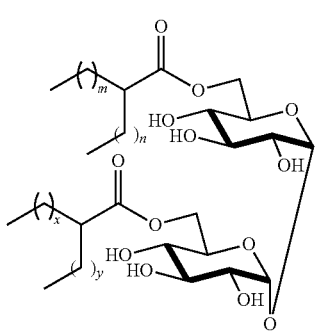

(I)

wherein m is an integer between 3 and 13; n is an integer between 3 and 13; x is an integer between 3 and 13; y is an integer between 3 and 13;

or a pharmaceutically acceptable salt and/or solvate and/or prodrug thereof, in the manufacture of a medicament for eliciting a pro-Th17 immune response.

There is also provided the use of a compound of formula (I):

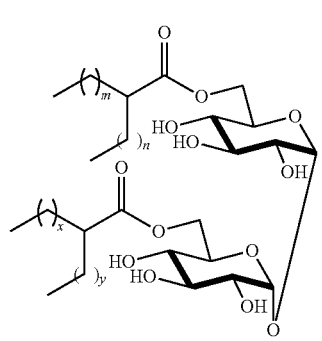

(I)

wherein m is an integer between 3 and 13; n is an integer between 3 and 13; x is an integer between 3 and 13; y is an integer between 3 and 13;

or a pharmaceutically acceptable salt and/or solvate and/or prodrug thereof, in the manufacture of an adjuvant.

The present invention provides a method for eliciting a pro-Th17 immune response in a subject, said method comprising the step of administering a compound of formula (I):

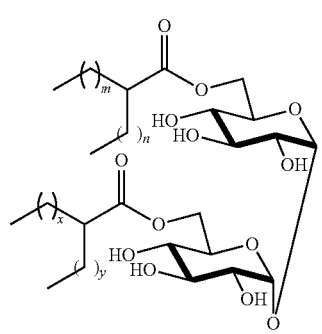

(I)

wherein m is an integer between 3 and 13; n is an integer between 3 and 13; x is an integer between 3 and 13; y is an integer between 3 and 13;

or a pharmaceutically acceptable salt and/or solvate and/or prodrug thereof, to the subject.

Also provided is a method of adjuvanting an immune response in a subject, said method comprising the step of administering a compound of formula (I):

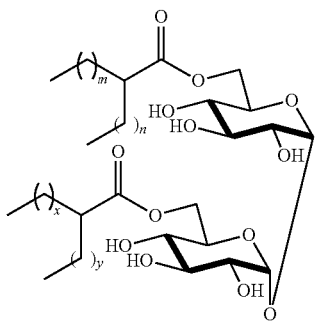

(I)

wherein m is an integer between 3 and 13; n is an integer between 3 and 13; x is an integer between 3 and 13; y is an integer between 3 and 13;

or a pharmaceutically acceptable salt and/or solvate and/or prodrug thereof, to the subject.

A further aspect of the invention is a compound of formula (I)

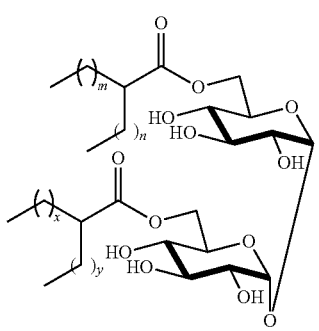

(I)

wherein m is an integer between 3 and 13; n is an integer between 3 and 13; x is an integer between 3 and 13; y is an integer between 3 and 13;

or a pharmaceutically acceptable salt or solvate thereof for use as a human medicament.

m is selected from 3, 4, 5, 6, 7, 8, 9, 10, 11, 12 or 13. Suitably m is 4, 5, 6, 7, 8 or 9, in particular between 4, 5, 6, 7, or 8, especially 5, 6, or 7, such as 6.

n is selected from 3, 4, 5, 6, 7, 8, 9, 10, 11, 12 or 13. Suitably n is 4, 5, 6, 7, 8 or 9, in particular between 4, 5, 6, 7, or 8, especially 5, 6, or 7, such as 6.

x is selected from 3, 4, 5, 6, 7, 8, 9, 10, 11, 12 or 13. Suitably x is 4, 5, 6, 7, 8 or 9, in particular between 4, 5, 6, 7, or 8, especially 5, 6, or 7, such as 6.

y is selected from 3, 4, 5, 6, 7, 8, 9, 10, 11, 12 or 13. Suitably y is 4, 5, 6, 7, 8 or 9, in particular between 4, 5, 6, 7, or 8, especially 5, 6, or 7, such as 6.

In some embodiments m and n are the same. In some embodiments m and x are the same. In some embodiments x and y are the same. In some embodiments n and y are the same. In some embodiments m, n, x and y are the same.

Suitably m+n+x+y is in the range of 16 to 34, in particular 18 to 30, especially 20 to 28, such as 22 to 26, for example 24.

In one embodiment m+n is 13 or less. In a second embodiment m+n is 11 or more.

In one embodiment x+y is 13 or less. In a second embodiment x+y is 11 or more.

Suitably m+n is 11, 12 or 13, in particular when m+n is 11, 12 or 13 and x+y is also 11, 12 or 13.

Suitably m and n differ by 4 or fewer, especially 3 or fewer, in particular 2 or fewer, such as by 1.

Suitably x and y differ by 4 or fewer, especially 3 or fewer, in particular 2 or fewer, such as by 1.

Suitably (m+n) and (x+y) differ by 4 or fewer, especially 3 or fewer, in particular 2 or fewer, such as by 1.

Compounds of formula (I) and (Ia), or the salt and/or solvate and/or prodrug thereof, may be formulated as a pharmaceutical composition with one or more pharmaceutically acceptable diluents or carriers.

Compounds of formula (I) and (Ia), or the salt and/or solvate and/or prodrug thereof, may be formulated as an immunogenic composition, together with at least one immunogen or antigen.

The invention also provides a kit comprising:
(i) a first composition comprising at least one compound of formula (I) or (Ia), or a salt and/or solvate and/or prodrug thereof; and
(ii) a second composition comprising at least one immunogen or antigen.

In some embodiments the compositions, kits and methods of the present invention may include a polynucleotide encoding the immunogen or antigen.

By the term immunogen is meant a polypeptide which is capable of eliciting an immune response. Suitably the immunogen is an antigen which comprises at least one B or T cell epitope. The elicited immune response may be an antigen specific B cell response, which produces neutralizing antibodies. The elicited immune response may be an antigen specific T cell response, which may be a systemic and/or a local response. The antigen specific T cell response may comprise a CD4+ T cell response, such as a response involving CD4+ T cells expressing a plurality of activation and differentiation surface markers, e.g. CD69, CD40L, CD45RO and/or CCR7; expressing a plurality of cytokines, e.g. IFNgamma, TNFalpha, IL-17 and/or IL2, demonstrating proliferating capabilities; and/or upregulating transcription factor expression, e.g. T-bet, RORgamma_t, GATA-3 or BCL-6. Alternatively, or additionally, the antigen specific T cell response comprises a CD8+ T cell response, such as a response involving CD8+ T cells expressing a plurality of activation and differentiation surface markers, e.g. CD69, CD40L, CD45RO, CD95, CD28 and/or CCR7; expressing a plurality of cytokines, e.g., IFNgamma, TNFalpha, IL-17 and/or IL2, demonstrating proliferating capabilities, and/or exhibiting cytotoxic activities towards antigen-presenting target cells.

The antigen may be derived (such as obtained from) from a human or non-human pathogen including, e.g., bacteria, virus, fungi, parasitic microorganisms or multicellular parasites which infect human and non-human vertebrates, or from a cancer cell or tumor cell. The antigen is suitably derived (such as obtained from) from a human pathogen including, bacteria, virus, fungi, parasitic microorganisms or multicellular parasites.

In one embodiment, the antigen is derived from, such as obtained from, *Mycobacterium* spp. (such as *Mycobacterium tuberculosis* (TB)). The antigen may comprise or consist of preparations derived from *Mycobacterium* spp., such as *Mycobacterium bovis* or *Mycobacterium tuberculosis*, in particular *Mycobacterium tuberculosis*.

Antigens of interest in the field of tuberculosis include Rv1196 and Rv0125. Rv1196 (described, for example, by the name Mtb39a in Dillon et al Infection and Immunity 1999 67(6): 2941-2950) is highly conserved, with 100% sequence identity across H37Rv, C, Haarlem, CDC1551, 94-M4241A, 98-R6041NH-RIF-EM, KZN605, KZN1435, KZN4207, KZNR506 strains, the F11 strain having a single point mutation Q30K (most other clinical isolates have in excess of 90% identity to H37Rv). Rv0125 (described, for example, by the name Mtb32a in Skeiky et al Infection and Immunity 1999 67(8): 3998-4007) is also highly conserved, with 100% sequence identity across many strains. Full length Rv0125 includes an N-terminal signal sequence which is cleaved to provide the mature protein.

In one embodiment the antigen is derived from Rv1196, such as comprise, such as consist of, a sequence having at least 70% identity to SEQ ID No: 1, such as at least 80%, in particular at least 90%, especially at least 95%, for example at least 98%, such as at least 99%. Typical Rv1196 related antigens will comprise (such as consist of) a derivative of SEQ ID No: 1 having a small number of deletions, insertions and/or substitutions. Examples are those having deletions of up to 5 residues at 0-5 locations, insertions of up to 5 residues at 0-5 five locations and substitution of up to 20 residues. Other derivatives of Rv1196 are those comprising (such as consisting of) a fragment of SEQ ID No: 1 which is at least 200 amino acids in length, such as at least 250 amino acids in length, in particular at least 300 amino acids in length, especially at least 350 amino acids in length.

In one embodiment the antigen is derived from Rv0125, such as an antigen comprising, such as consist of, a sequence having at least 70% identity to SEQ ID No: 2, such as at least 80%, in particular at least 90%, especially at least 95%, for example at least 98%, such as at least 99%. Typical Rv0125 related antigens will comprise (such as consist of) a derivative of SEQ ID No: 2 having a small number of deletions, insertions and/or substitutions. Examples are those having deletions of up to 5 residues at 0-5 locations, insertions of up to 5 residues at 0-5 five locations and substitution of up to 20 residues. Other derivatives of Rv0125 are those comprising (such as consisting of) a fragment of SEQ ID No: 2 which is at least 150 amino acids in length, such as at least 200 amino acids in length, in particular at least 250 amino acids in length, especially at least 300 amino acids in length. Particular derivatives of Rv0125 are those comprising (such as consisting of) the fragment of SEQ ID No: 2 corresponding to residues 1-195 of SEQ ID No: 2. Further immunogenic derivatives of Rv0125 are those comprising (such as consisting of) the fragment of SEQ ID No: 2 corresponding to residues 192-323 of SEQ ID No: 2. Particularly preferred Rv0125 related antigens are derivatives of SEQ ID No: 2 wherein at least one (for example one, two or even all three) of the catalytic triad have been substituted or deleted, such that the protease activity has been reduced and the protein more easily produced—the catalytic serine residue may be deleted or substituted (e.g. substituted with alanine) and/or the catalytic histidine residue may be deleted or substituted and/or substituted the catalytic aspartic acid residue may be deleted or substituted. Especially of interest are derivatives of SEQ ID No: 2 wherein the catalytic serine residue has been substituted (e.g. substituted with alanine). Also of interest are Rv0125 related antigens which comprise, such as consist of, a sequence having at least 70% identity to SEQ ID No: 2, such as at least 80%, in particular at least 90%, especially at least 95%, for example at least 98%, such as at least 99% and wherein at least one of the catalytic triad have been substituted or deleted or those comprising, such as consisting of, a fragment of SEQ ID No: 2 which is at least 150 amino acids in length, such as at least 200 amino acids in length, in particular at least 250 amino acids in length, especially at least 300 amino acids in length and wherein at least one of the catalytic triad have been substituted or deleted. Further immunogenic derivatives of Rv0125 are those comprising (such as consisting of) the fragment of SEQ ID No: 2 corresponding to residues 192-323 of SEQ ID No: 2 wherein at least one (for example one, two or even all three) of the catalytic triad have been substituted or deleted. Particular immunogenic derivatives of Rv0125 are those comprising (such as consisting of) the fragment of SEQ ID No: 2 corresponding to residues 1-195 of SEQ ID No: 2 wherein the catalytic serine residue (position 176 of SEQ ID No: 2) has been substituted (e.g. substituted with alanine).

Suitably the antigen will comprise, such as consist of, a sequence having at least 70% identity to SEQ ID No. 3, such as at least 80%, in particular at least 90%, especially at least 95%, such as at least 98%, for example at least 99%. Typical M72 related antigens will comprise, such as consist of, a derivative of SEQ ID No: 3 having a small number of deletions, insertions and/or substitutions. Examples are those having deletions of up to 5 residues at 0-5 locations, insertions of up to 5 residues at 0-5 five locations and substitution of up to 20 residues. Other derivatives of M72 are those comprising, such as consisting of, a fragment of SEQ ID No: 3 which is at least 450 amino acids in length, such as at least 500 amino acids in length, such as at least 550 amino acids in length, such as at least 600 amino acids in length, such as at least 650 amino acids in length or at least 700 amino acids in length. As M72 is a fusion protein derived from the two individual antigens Rv0125 and Rv1196, any fragment of at least 450 residues will comprise a plurality of epitopes from the full length sequence (Skeiky et al J. Immunol. 2004 172:7618-7628; Skeiky Infect. Immun. 1999 67(8):3998-4007; Dillon Infect. Immun. 1999 67(6):2941-2950).

M72 related antigen will comprise, such as consist of, a sequence having at least 70% identity to SEQ ID No. 3, such as at least 80%, in particular at least 90%, especially at least 95%, such as at least 98%, for example at least 99%.

Typical M72 related antigens will comprise, such as consist of, a derivative of SEQ ID No: 3 having a small number of deletions, insertions and/or substitutions. Examples are those having deletions of up to 5 residues at 0-5 locations, insertions of up to 5 residues at 0-5 five locations and substitution of up to 20 residues.

In particular embodiments the M72 related antigen will comprise residues 2-723 of SEQ ID No. 3, for example comprise (or consist of) SEQ ID No. 3 or comprise (or consist) of SEQ ID No. 4.

Tuberculosis antigens are most suitably utilised in the form of a polypeptide, but may alternatively be provided in the form of a polynucleotide encoding said polypeptide.

The compounds of formula (I) or (Ia), or the salt and/or solvate and/or prodrug thereof, may be together with at least one other therapeutically active agent.

There is also provided a process for preparing a pharmaceutical composition which comprises admixing a compound of formula (I), or a pharmaceutically acceptable salt thereof, with one or more pharmaceutically acceptable diluents or carriers.

Formulation of pharmaceutically-acceptable excipients and carrier solutions is well-known to those of skill in the art, as is the development of suitable dosing and treatment regimens for using the particular compositions described herein in a variety of treatment regimens. The compounds of formula (I) or their pharmaceutically acceptable salts and/or solvates and/or prodrugs thereof may be administered by any convenient method, e.g., oral, parenteral, intravenous, buccal, sublingual, rectal, transdermal or intradermal administration, intranasal, intratympanic, intracochlear or intramuscular administration. Other routes of administration include via the mucosal surfaces.

Typically the compounds of formula (I) or (Ia), or pharmaceutically acceptable salts and/or solvates and/or prodrugs thereof, are administered parenterally, such as intramuscularly or subcutaneously.

Salts of the compounds of formula (I) or (Ia) include pharmaceutically acceptable salts and salts which may not be pharmaceutically acceptable but may be useful in the preparation of compounds of formula (I) and pharmaceutically acceptable salts thereof. Salts may be derived from certain inorganic or organic acids, or certain inorganic or organic bases. For a review on suitable salts see for example Berge et al., *J. Pharm. Sci.*, 66:1-19 (1977).

Solvates of the compounds of formula (I) or (Ia) include pharmaceutically acceptable solvates and solvates which may not be pharmaceutically acceptable but may be useful in the preparation of the compounds of formula (I) or (Ia) and pharmaceutically acceptable solvates thereof. Pharmaceutically acceptable solvates include hydrates.

Salts and hydrates may be provided in stoichiometric and non-stoichiometric amounts.

A "pro-Th17 response" is an immune response which is associated with the development of Th17 lymphocytes, producing cytokines from the IL17 protein family (notably IL17A, IL17F), IL-22 and/or IL-21, and expressing the transcription factor RORgamma_t. Suitably the pro-Th17 response involves the elicitation of cytokines which are associated with Th17, in particular TNF-alpha, IL-6, IL-23 and IL-1beta. The pro-Th17 response desirably involves the elicitation of Th17 cells and/or IL-17 cytokines in the systemic blood circulation and/or in the mucosal tissues.

As used herein, a "subject" is any mammal, including but not limited to humans, non-human primates, farm animals such as cattle, sheep, pigs, goats and horses; domestic animals such as cats, dogs, rabbits; laboratory animals such as mice, rats and guinea pigs that exhibit at least one symptom associated with a disease, have been diagnosed with a disease, or are at risk for developing a disease. The term does not denote a particular age or sex. Suitably the subject is a human subject.

Isotopically-labelled compounds which are identical to those recited in formula (I) but for the fact that one or more atoms are replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment") are also contemplated for the uses and method of the invention. Examples of isotopes that can be incorporated into the compounds of the invention include isotopes of hydrogen, carbon, nitrogen, oxygen, fluorine, iodine and chlorine such as $^2$H (deuterium), $^3$H, $^{11}$C, $^{13}$C, $^{14}$C $^{18}$F, $^{123}$I or $^{125}$I, which may be naturally occurring or non-naturally occurring isotopes. Compounds of formula (I) or (Ia), or a salt and/or solvate and/or prodrug and pharmaceutically acceptable salts of said compounds, that contain the aforementioned isotopes and/or other isotopes of other atoms are contemplated for use for the uses and method of the present invention. Isotopically labelled compounds of the present invention, for example those into which radioactive isotopes such as $^3$H or $^{14}$C have been incorporated, are useful in drug and/or substrate tissue distribution assays. Tritiated, i.e. $^3$H, and carbon-14, i.e. $^{14}$C, isotopes are particularly preferred for their ease of preparation and detectability. $^{11}$C and $^{18}$F isotopes are particularly useful in PET (positron emission tomography).

Since the compounds of formula (I) or (Ia), or pharmaceutically acceptable salts and/or solvates and/or prodrugs thereof, are intended for use in pharmaceutical compositions it will readily be understood that it is preferably provided in substantially pure form, for example at least 60% pure, more suitably at least 75% pure and preferably at least 85%, especially at least 98% pure (% are on a weight for weight basis). Impure preparations of the compounds may be used for preparing the more pure form used in the pharmaceutical compositions.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent, such as water for injection or saline, prior to administration.

The composition may contain from 0.001% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.001 mg to 10 mg, for example from 0.01 mg to 1 mg, of the active material, depending on the method of administration.

In one aspect of the invention, the compounds of formula (I) or (Ia) are provided in the form of an aqueous adjuvant composition.

When formulated, the compound of formula (I) or (Ia), or pharmaceutically acceptable salts and/or solvates and/or prodrugs thereof, may be provided with a suitable carrier such as liposomes. The term 'liposome' is well known in the art and defines a general category of vesicles which comprise one or more lipid bilayers surrounding an aqueous space. Liposomes thus consist of one or more lipid and/or phospholipid bilayers and can contain other molecules, such as proteins or carbohydrates, in their structure. Because both lipid and aqueous phases are present, liposomes can encapsulate or entrap water-soluble material, lipid-soluble material, and/or amphiphilic compounds. Liposome size may vary from 30 nm to several um depending on the phospholipid composition and the method used for their preparation. In particular embodiments of the invention, the liposome size will be in the range of 50 nm to 500 nm and in further embodiments 50 nm to 200 nm. Optimally, the liposomes should be stable and have a diameter of ~100 nm to allow sterilization by filtration.

Suitably, the compositions used in the present invention have a human dose volume of between 0.05 ml and 1 ml, such as between 0.1 and 0.5 ml, in particular a dose volume of about 0.5 ml, or 0.7 ml. The volumes of the compositions used may depend on the delivery route and location, with smaller doses being given by the intradermal route. Smaller volumes may also be used for juvenile subjects, such as human infants or children.

The pH of a liquid preparation is adjusted in view of the components of the composition and necessary suitability for administration to the subject. Suitably, the pH of a liquid mixture is at least 4, at least 5, at least 5.5, at least 5.8, at least 6. The pH of the liquid mixture may be less than 9, less than 8, less than 7.5 or less than 7. In other embodiments, pH of the liquid mixture is between 4 and 9, between 5 and 8, such as between 5.5 and 8. In a further embodiment, a buffer is added to the composition.

It is well known that for parenteral administration solutions should have a pharmaceutically acceptable osmolality to avoid cell distortion or lysis. A pharmaceutically acceptable osmolality will generally mean that solutions will have an osmolality which is approximately isotonic or mildly hypertonic. Suitably the compositions of the present invention when reconstituted will have an osmolality in the range of 250 to 750 mOsm/kg, for example, the osmolality may be in the range of 250 to 550 mOsm/kg, such as in the range of 280 to 500 mOsm/kg.

Osmolality may be measured according to techniques known in the art, such as by the use of a commercially available osmometer, for example the Advanced® Model 2020 available from Advanced Instruments Inc. (USA).

A desired osmolality may be achieved by the inclusion of salts or through the use of non-ionic isotonicity agents. In one embodiment of the present invention, suitable non-ionic isotonicity agents are polyols, sugars (in particular sucrose, fructose, dextrose or glucose) or amino acids such as glycine. In one embodiment the polyol is a sugar alcohol especially a C3-6 sugar alcohol. Exemplary sugar alcohols include glycerol, erythritol, threitol, arabitol, xylitol, ribitol, sorbitol, mannitol, dulcitol and iditol. In a specific example of this embodiment, a suitable non-ionic isotonicity agent is sorbitol. In a particular embodiment of the invention the non-ionic isotonicity agent in the compositions of the invention is sucrose and/or sorbitol.

In a further embodiment of the invention, there is provided a kit comprising (i) a lyophilised composition comprising an antigen or antigenic preparation and (ii) an aqueous adjuvant composition as described herein.

Compounds of formula (I) and (Ia) may be prepared by the following general methods: Triflate route synthesized according to: Johnson et al (1998).

Accordingly, there is provided a process for the preparation of a compound of formula (I) which process comprises the deprotection of a compound of formula (II):

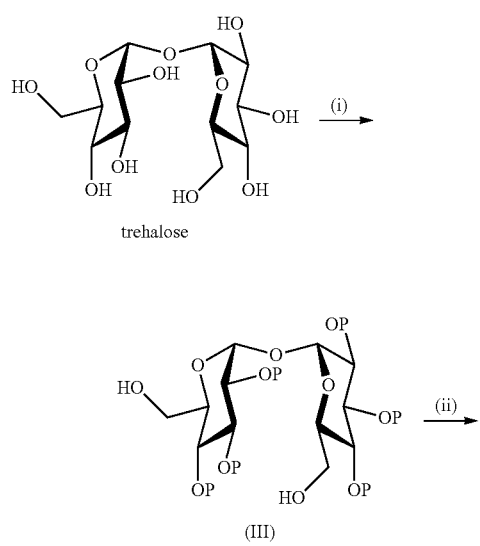

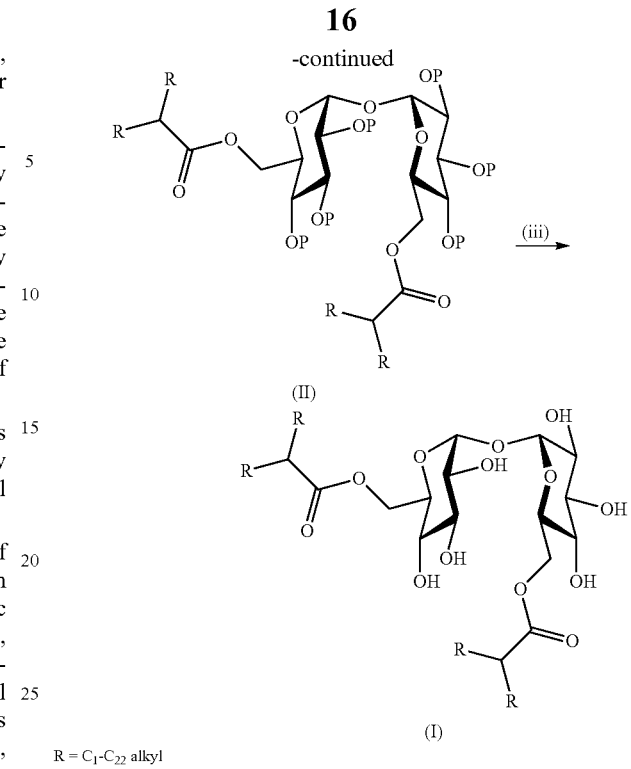

$R = C_1\text{-}C_{22}$ alkyl

Trehalose is exposed to a hydroxy-protecting agent (P) such as bis(trimethylsilyl)acetamide under basic conditions (such as in the presence of N-methyl pyrrolidinone) with an organic catalyst such as tetra-n-butylammonium fluoride (TBAF) to form a protected trehalose derivative such as a TMS-protected trehalose derivative. The protected trehalose derivative is exposed to a base such as $K_2CO_3$ in an alcoholic solvent such as methanol to obtain a compound of formula (III).

A compound of formula (III) is exposed to a hydroxy-activating agent such as triflic anhydride in a basic solvent such as pyridine. Following activation of the free hydroxy group, to form the corresponding triflate, a compound of formula (III) is exposed to a suitable carboxylic acid, such as $(R)_2CHCOOH$ (compound c) in the presence of a salt such as KOTMS in a polar solvent such as THF and is heated to form a compound of (II).

The compound of formula (II) is exposed to a deprotecting agent such as an acid e.g. TFA or AcOH in an aqueous polar solvent such as aqueous THF to form compounds of formula (I).

Compound c can be made by the following process:

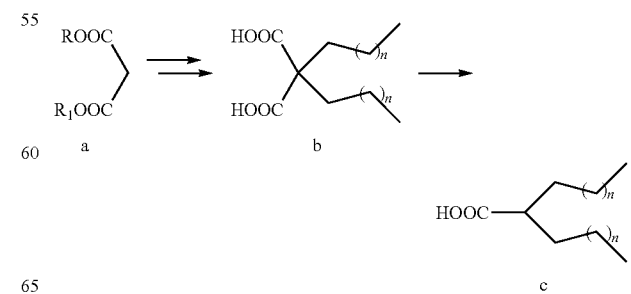

Diester a (wherein R and $R_1$ may be the same or different and may each be independently selected from Me, Et, Pr and Bu) is exposed to an alkyl halide, such as an alkyl bromide, in the presence of sodium metal and an alcoholic solvent such as butanol or ethanol. The intermediate diester that forms is hydrolysed under basic conditions (such as in the presence NaOH or KOH) to form diacid b (wherein n may be 5, 6 or 7). Decarboxylation of diacid b under heated conditions provides monoacid c.

By the term prodrug is meant herein a derivative of the compound of formula (I) or (Ia) which is metabolised in the body to produce the compound of formula (I) or (Ia).

It is to be understood that the present invention encompasses all isomers of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

References to compounds of formula (I) should be taken to apply to compounds of formula (Ia) unless the context requires otherwise.

EXAMPLES

Synthesis of Compounds

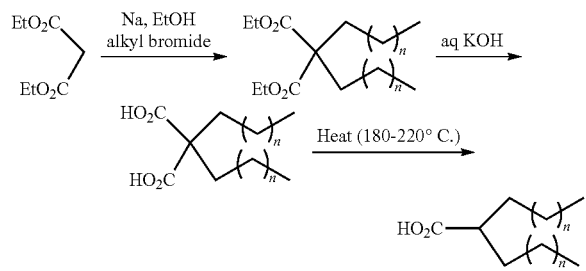

To synthesize the test compounds, the appropriate acids were salted with an excess of KOTMS in THF and then the potassium salts were precipitated with acetonitrile, filtered and collected for use in subsequent coupling reactions. The 'Number of C' column corresponds to the total number of carbons in the symmetrical alpha branched acid.

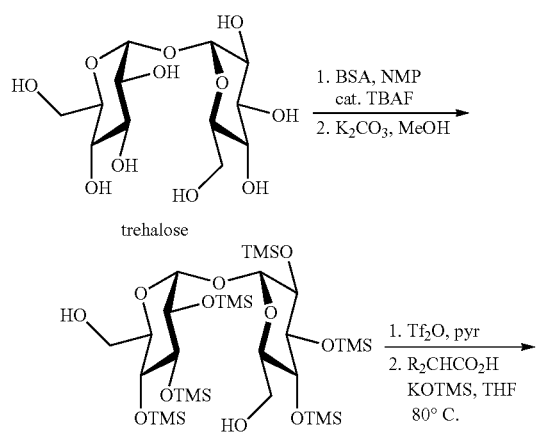

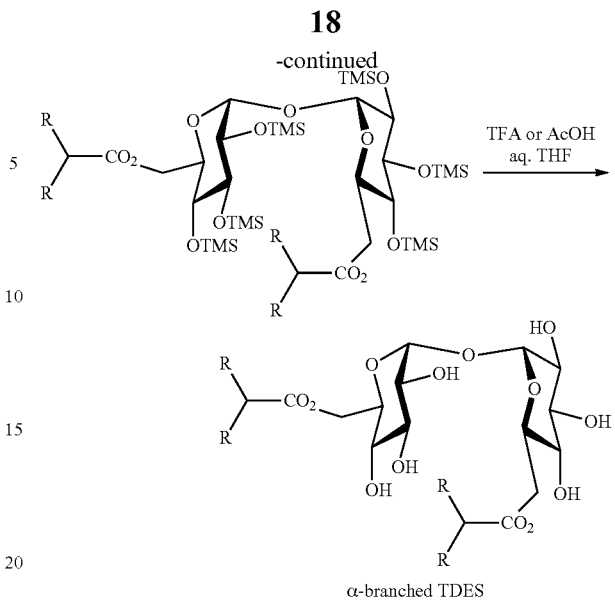

The appropriately protected trehalose was treated with triflic anhydride to provide the di-triflate, which was then coupled with the potassium salts of the appropriate acid prepared above.

Removal of the silyl protecting groups using THF:AcOH:$H_2O$ provided the target compounds after chromatography. Compound identity was confirmed by $^1H$ NMR and high resolution mass spectrometry. Compounds conformed to literature data (Yamamoto et al (2013)) or were otherwise as expected.

| Compound | n | m | x | y | Number of C |
|---|---|---|---|---|---|
| B4 | 0 | 0 | 0 | 0 | 4 |
| B6 | 1 | 1 | 1 | 1 | 6 |
| B8 | 2 | 2 | 2 | 2 | 8 |
| B10 | 3 | 3 | 3 | 3 | 10 |
| B12 | 4 | 4 | 4 | 4 | 12 |
| B14 | 5 | 5 | 5 | 5 | 14 |
| B16 | 6 | 6 | 6 | 6 | 16 |
| B18 | 7 | 7 | 7 | 7 | 18 |
| B20 | 8 | 8 | 8 | 8 | 20 |
| B22 | 9 | 9 | 9 | 9 | 22 |
| B24 | 10 | 10 | 10 | 10 | 24 |
| B26 | 11 | 11 | 11 | 11 | 26 |
| B28 | 12 | 12 | 12 | 12 | 28 |
| B30 | 13 | 13 | 13 | 13 | 30 |
| B32 | 14 | 14 | 14 | 14 | 32 |
| B34 | 15 | 15 | 15 | 15 | 34 |
| B36 | 16 | 16 | 16 | 16 | 36 |
| B38 | 17 | 17 | 17 | 17 | 38 |
| B40 | 18 | 18 | 18 | 18 | 40 |
| B42 | 19 | 19 | 19 | 19 | 42 |
| B44 | 20 | 20 | 20 | 20 | 44 |
| B46 | 21 | 21 | 21 | 21 | 46 |

Biological Testing of Compounds

Example 1—Cytokine Production from Human PBMCs

Method

TDM (trehalose-6,6'-dimycolate) was obtained from Sigma. TDB (6,6'-dibehenoyl-α,α'-trehalose) was obtained from Avanti Polar Lipids. MMG (glycerol monomycolate) was prepared according to the procedure of Andersen et. al. sTDCM (synthetic trehalose dicorynomycolate) was obtained from Sigma-Aldrich (Catalog Number S3452).

PBMCs were obtained via leukapheresis from normal donors (AllCells, Berkeley, CA). Upon receipt PBMCs were repeatedly washed in 1×PBS and cryopreserved in freezing media (50% RPMI, 40% FCS, 10% DMSO) for future use. For assay, cells were immediately thawed into RPMI media, 10% heat inactivated FBS, 1× penicillin/streptomycin/glutamine (complete media), washed once and resuspended to the desired cell concentration in complete media. Cells were treated with the indicated compound concentrations by addition to plates containing serial dilution of the stock compound in diluent (50% isopropanol/50% isooctane). Compounds were applied, 20 ul final volume, to the bottom of a tissue culture plate and solvent was allowed to fully evaporate (i.e. plate coating) before cell addition.

Supernatants were harvested from treated cells 18-24 h post cell application. Supernatants were analyzed using a Luminex multiplex panel for analytes TNFα, IL-1β, IL-6, IFNγ, IL-12p70 and IL-23 per the manufacturer's instructions.

Results

IL-12 or IFNγ were not detected in response to any compound (data not shown).

Figure 2:
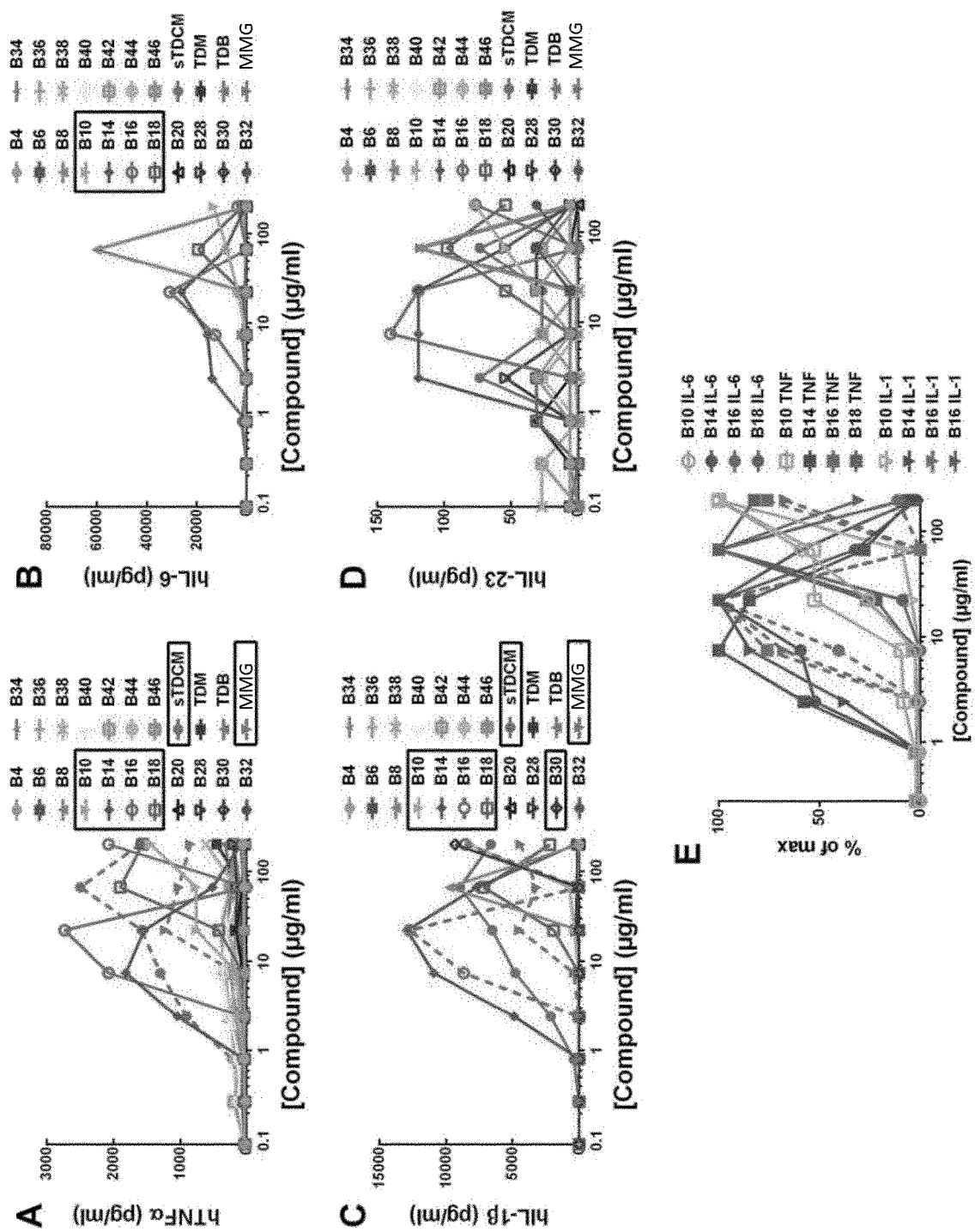
FIGS. 2A-E: Cytokine production (hTNFα (A), hIL6 (B), hIL1β (C) and hIL23 (D)) from human PBMCs in response to the compounds of the invention. Graph in E demonstrates the percent maximum cytokine production of IL6 (•) TNFα (■) or IL1β (▼) of any given dose of the example compounds 4, 6, 7 or 8.

Low levels of IL-23 were measured for the highly active B14 and B16 compounds (FIG. 2D).

IL6 and IL1β were readily detected with the "mid-length" acyl chain compound, B10, B14, B16 and B18 (FIG. 2B). When the TNFα, IL6 and IL1β dose response curves for the mid-range compounds were compared head to head (FIG. 2E), very similar dose trends for each compound were seen among the cytokines. These results suggest that for these four particularly active compounds induce similar kinetics for all cytokines tested.

Overall the results show that influential Th17-promoting cytokine activity in human PBMCs is greatest in those compounds in the B10 to B32 range.

Example 2—Cytokine Production from Mouse Raw Cells

Method

The compounds were screened for their ability to induce TNFα from the mouse Raw cell line. An aim of this study was to determine if species specific differences in responses to compounds may be observed.

Results

Figure 4:
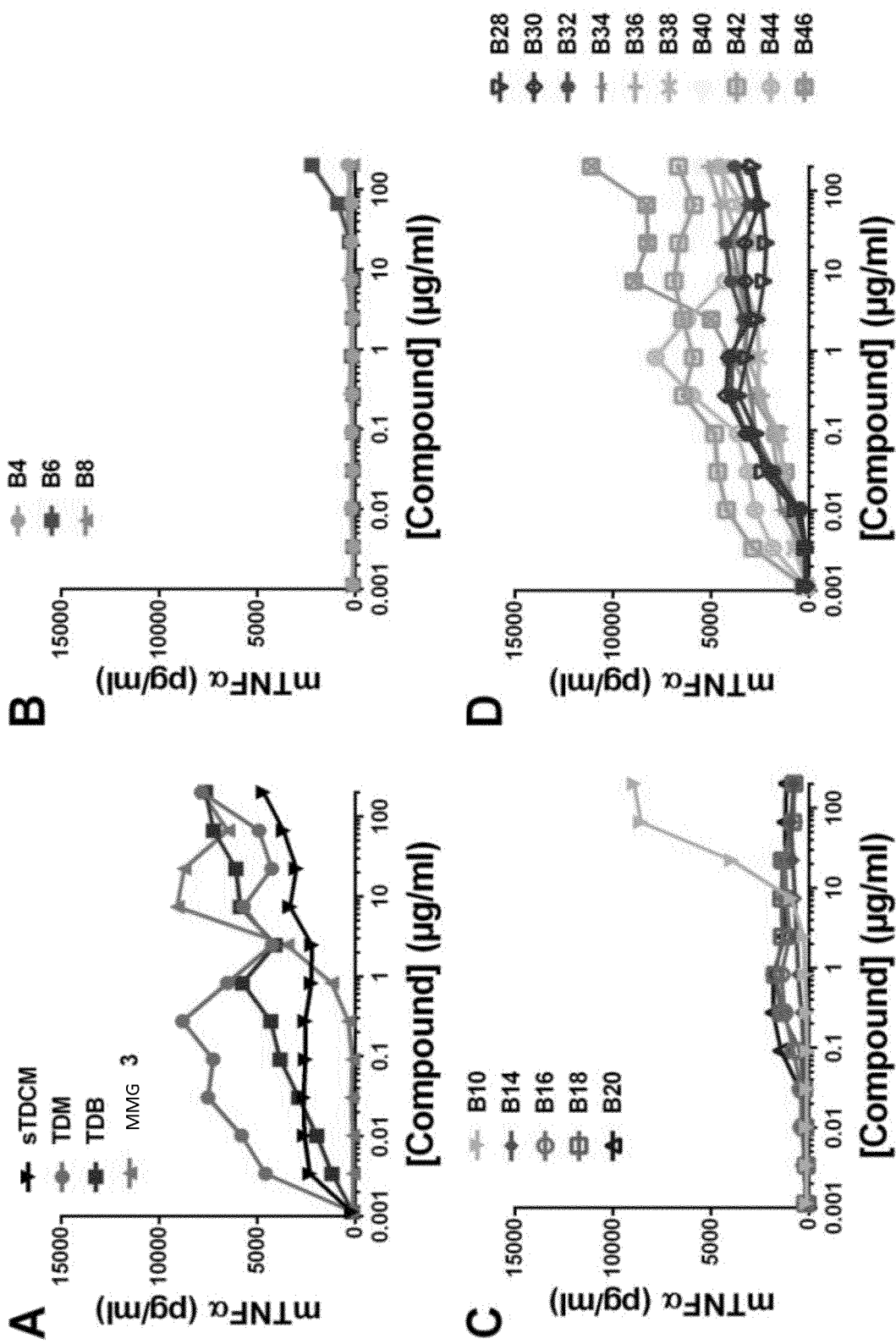
FIGS. 4A-D: Cytokine production (mTNFα) from mouse Raw cells in response to the compounds of the invention.

The natural agonist TDM and the synthetic unbranched chain TDB were more potent in the mouse cell line as compared to human cells; demonstrating equivalent potency as the synthetic, racemic sTDCM but higher efficacy/peak levels (FIG. 4A). MMG demonstrated some activity in the mouse cell line, eventually inducing equivalent levels of TNFα as the other compounds, but it was over 100 fold less potent than sTDCM. MMG/sTDCM potency difference was closer to 10 fold in the human cells.

For the synthetic compounds, the shortest chain compounds (B4, B6 and B8) elicited very little TNFα (FIG. 4B). The "mid" acyl chain length compounds were active on mouse cells but did not induce the highest levels of cytokines as previously noted in the human PBMC system. However, similar to the human PBMCs they induced peak cytokine responses at lower doses and dropped off in response at higher concentrations (FIG. 4C). In contrast to the response in human PBMCs, in murine Raw cells the highest activity was demonstrated with longer (B28 and greater) acyl chain compounds (FIG. 4D).

Together, these results underscore the differences between human and mouse response the compounds.

BIBLIOGRAPHY

Andersen et al., *Journal of Immunology*, 2009, 182:424-32
Decout et al., *PNAS*, 2017, 114(10):2675-2680
Foster et al., *Journal of Medicinal Chemistry*, 2018, 61(3): 1045-1060
Huber et al., *Innate Immunity*, 2016, 22(6):405-418
Kahn et al., *ChemBioChem*, 2011, 12:2572-2576
Kallerup et al., *European Journal of Pharmaceutics and Biopharmaceutics*, 2015, 90:80-89
Johnson et al., *Journal of Carbohydrate Chemistry*, 1998, 17:969-974
Van der Peet et al., *Chemical Communications*, 2015, 51:5100-5103
Van der Peet et al., *Organic & Biomolecular Chemistry*, 2016, 14:9267-9277
Yamamoto et al., *Journal of Medicinal Chemistry*, 2013, 56(1):381-385

The invention claimed is:

1. A compound of the formula:

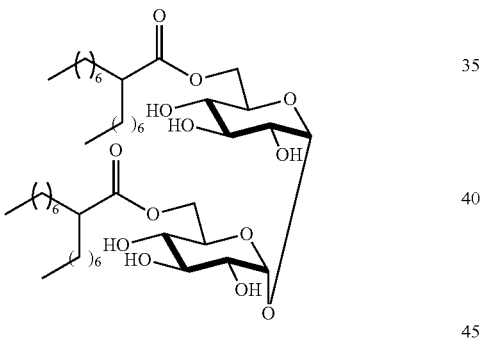

or a pharmaceutically acceptable salt thereof.

* * * * *